United States Patent [19]

Cully et al.

[11] Patent Number: 5,527,703
[45] Date of Patent: Jun. 18, 1996

[54] DNA ENCODING GLUTAMATE GATED CHLORIDE CHANNELS

[75] Inventors: Doris F. Cully, Scotch Plains; Joseph P. Arena, West Orange; Ken K. Liu, Laurence Harbor; Demetrios Vassilatis, Edison, all of N.J.

[73] Assignee: Merck & Co., Inc., Rahway, N.J.

[21] Appl. No.: 249,112

[22] Filed: May 25, 1994

[51] Int. Cl.$^6$ .......................... C12N 1/20; C12N 15/00; C07H 21/04
[52] U.S. Cl. .................. 435/252.3; 435/320.1; 536/23.5
[58] Field of Search ...................... 435/69.1, 240.2, 435/252.33, 254.2, 7.8; 530/350, 388.1; 514/12

[56] References Cited

U.S. PATENT DOCUMENTS

5,385,831  1/1995  Mulvihill et al. ................. 435/69.1

FOREIGN PATENT DOCUMENTS

WO92/22652  12/1992  WIPO.
WO93/07161  4/1993  WIPO.

OTHER PUBLICATIONS

Hallmann et al Nature 342:643–648 (1989).
Arena, J. P. "Expression of Caenorhabditis elegans mRNA in Xenopus oocytes: A Model System to Study the Mechanism of Action of Avermectins", Parasitology Today, vol. 10, No. 1, 1994 pp. 35–37.
Harlow et al. "Antibodies" A Laboratory Manual; Chap. 5; pp. 92–115; Cold Spring Harbor Laboratory 1988.
Julius, "Molecular Characterization of a Functional cDNA Encoding the Serotonin 1c Receptor", Science, vol. 241; Jul. 1988; pp. 558–564.
Zufall et al. "The Insecticide Avermectin B1a Activates a Chloride Channel in Crayfish Muscle Membrane", J. Exp. Biol. 142, 191–205 (1989).
Arena, J., et al., Expression of a glutamate-activated chloride current in Xenopus oocytes injected with Caenorhabditis elegans RNA: evidence for modulation by avenmectin, Molecular Brain Research, 15, pp. 339–348 (1992).
Ffrrench–Constant, R., et al. Molecular cloning and transformation of cyclodiene resistance in Drosophila; An invertebrate y–aminobutyric acid subtype A receptor locus, Proc. Natl. Acad. Sci. USA, vol. 88, pp. 7209–7213 (1991).
Ffench–Constant, R, et al. A point mutation in a Drosophia GABA receptor confers insecticide resistance, Nature, vol. 363, pp. 449–451 (1993).
Henderson, J. et al., Characterization of a putative y–aminobutyric acid (gaba) receptor B subunit gene from Drosophila melanogaster, vol. 193, No. 2, pp. 474–482 (1993).
Thompson, M. et al., Cloning and sequencing of the cyclodiene insecticide resistance gene from the yellow fever mosquito Aedes aegypti, vol. 325, No. 3, pp. 187–190 (1993).
Arena, J. et al., Avermectin–sensitive chloride currents induced by caenorhabditis elegans RNA in xenopus oocytes, Molecular Pharm., 40, pp. 368–374 (1991).
Harvey, R. et al., Sequence of functional invertebrate GABAA receptor subunit which can form a chimeric receptor with a vertebrate a subunit. The EMBO Jour., vol. 10, No. 11 pp. 3239–3245 (1991).
Hutton, M. L. et al., A novel invertebrate GABAA receptor–like polypeptide sequence and pattern of gene expression, FEBS 12670, vol. 326, No. 1,2,3, pp. 112–116 (1993).
Zaman, S. et al., Unusual effects of benzodiazepines and cyclodiene insecticides on an expressed invertebrate GABAA receptor, FEBS 11356, vol. 307, No. 3, pp. 351–354 (1992).

*Primary Examiner*—Robert A. Wax
*Assistant Examiner*—Lisa J. Hobbs
*Attorney, Agent, or Firm*—Jack L. Tribble; Christine E. Carty

[57] ABSTRACT

DNAs encoding glutamate and avermectin-sensitive chloride channels have been cloned and characterized. The individual alpha and beta subunits are capable of forming homomeric and heteromeric channels selectively opened with either avermectin or glutamate. The cDNA's have been expressed in recombinant host cells which produce active recombinant protein. The recombinant protein is also purified from the recombinant host cells. In addition, the recombinant host cells are utilized to establish a method for identifying modulators of the receptor activity, and receptor modulators are identified. Receptor modulators are useful as insecticides and anthelminthic agents.

6 Claims, 9 Drawing Sheets

TAACCCCTCAATACTGCATAAATTGGCAATTATATATTTTTGCTTCGGCAA
TGGCTACCTGGATTGTCGGAAAGCTGATCATTGCATCTTTAATTTTGGGAA
TACAAGCCCAACAAGCTAGAACGAAATCACAAGATATTTTCGAAGATGA
TAATGATAATGGAACGACTACACTGGAATCGCTAGCCAGATTAACATCC
CCGATTCACATTCCAATTGAACAACCTCAAACATCGGACTCAAAAATTCT
AGCTCATCTTTTCACATCTGGATACGATTTCCGAGTGCGACCTCCAACAG
ATAATGGAGGACCAGTTGTGGTTTCAGTTAACATGCTCCTTCGAACTATTT
CAAAGATAGATGTTGTGAATATGGAGTATAGTGCTCAATTGACATTGCGA
GAGAGTTGGATTGACAAGAGACTCAGCTACGGAGTAAAAGGAGATGGTC
AGCCAGATTTTGTGATTCTCACTGTTGGACATCAAATTTGGATGCCCGAC
ACGTTTTTCCCGAATGAGAAACAAGCTTACAAGCATACGATTGATAAGCC
GAATGTATTGATTCGAATACACAATGATGGTACAGTATTGTACTCTGTTC
GTATTTCACTAGTCCTCTCTTGCCCAATGTATCTACAGTACTATCCAATGG
ATGTTCAACAGTGTTCCATTGATCTTGCATCGTATGCCTACACTACAAAA
GATATCGAATATTTGTGGAAAGAGCATTCACCACTTCAGTTAAAGGTTGG
ATTATCAAGCTCGTTGCCTTCATTCCAGTTGACTAATACTTCAACGACATA
TTGCACCAGTGTAACAAACACTGGCATTTATTCCTGTTTGCGAACTACTAT
TCAGTTAAAGAGAGAGTTCAGTTTTTACCTTCTCCAACTCTACATCCCGTC
ATGCATGCTAGTCATCGTATCCTGGGTTTCATTTTGGTTTGATCGAACTGC
AATCCCGGCTCGTGTCACCCTCGGAGTCACCACGCTGCTTACAATGACAG
CTCAATCAGCCGGTATCAATTCACAACTACCTCCAGTTTCCTATATCAAG
GCGATTGATGTCTGGATTGGTGCATGTATGACATTCATTTCTGCGCGTTG
TTGGAGTTTGCATTGGTAAATCATATAGCTAACAAGCAGGGTGTTGAGAG
AAAAGCTCGAACTGAAAGAGAGAAAGCTGAAATTCCACTTCTTCAAAAT
TTGCACAATGATGTTCCCACAAAGGTTTTCAATCAAGAGGAAAAAGTAA
GGACAGTTCCACTGAATCGCCGGCAAATGAATAGCTTCTTGAATTTGCTC
GAGACAAAAACCGAATGGAATGACATATCAAAACGAGTCGATCTTATTT
CTCGAGCCCTGTTTCCTGTTCTATTTTTTGTTTTAACATTTTGTACTGGTCT
CGTTTTGGCCAGCAGAACGTATTATTTTAGATTTGTAAATCGAATAAGTTT
TTGTTTTATGGCAAAAATGATCGAGAATGCTTTTGATTTAATCTGAATGAA
ACTGTTTAAAAAATTAAAAAAAAAAAAAAAAAAA

FIG.1

```
CAATAATGCAATTATGACTACACCTAGTTCATTTTCAATTCTGCTCCTCCT
GCTACTGATGCCCGTCGTCACAAATGGCGAGTACAGTATGCAATCGGAG
CAGGAGATTCTAATGCGTTGCTCAAAAATTATGACATGCGGGTACGGCC
ACCACCGGCCAACTCATCAACGGAAGGTGCTGTCAATGTTCGTGTTAATA
TTATGATTCGGATGCTATCGAAAATTGATGTAGTTAATATGGAATATTCA
ATTCAACTAACATTCCGCGAGCAATGGATAGATCCTCGACTGGCCTATGA
AAATTTGGGTTTCTACAATCCTCCGGCATTTCTCACAGTCCCACATGTTAA
AAAGAGTCTATGGATTCCTGACACATTCTTTCCCACCGAAAAAGCAGCTC
ATAGACATTTGATTGATATGGAAACATGTTCTTGAGGATATATCCGGAT
GGAAAAATCCTCTACAGTTCCCGGATAAGTTTGACAAGTTCCTGCCCAAT
GCGTCTCCAACTCTACCCACTCGACTATCAATCGTGTAACTTTGATCTTGT
CAGCTACGCGCACACAATGAATGATATCATGTACGAGTGGGATCCATCA
ACACCAGTTCAACTGAAACCCGGCGTTGGCTCGGATCTTCCCAATTTTAT
ACTCAAAAACTACACAACAAATGCAGATTGCACAAGCCACACGAACAC
AGGATCATATGGATGTCTCCGAATGCAACTTTGTTCAAACGGCAATTCA
GTTATTACTTGGTACAACTGTATGCTCCAACCACTATGATTGTGATTGTCT
CATGGGTTTCATTTGGATTGATCTTCATTCAACTGCTGGACGTGTCGCTTT
AGGAGTCACTACGCTTCTTACAATGACTACAATGCAATCTGCAATCAACG
CCAAGCTTCCACCAGTTAGCTACGTAAAAGTTGTGGATGTCTGGCTTGGA
GCGTGCCAAACATTTGTATTCGGAGCACTTCTGGAATACGCATTTGTCAG
TTATCAAGATAGTGTCCGGCAAAATGACAGGTCAAGAGAGAAAGCTGCA
AGGAAGGCGCAGAGAAGGAGAGAAAGTTGGAAATGGTGGATGCAGAA
GTCTATCAGCCACCGTGCACCTGTCATACTTTCGAAGCCCGCGAGACATT
CCGTGACAAAGTCCGCCGTTACTTCACAAAACCAGATTATCTACCGGCAA
AAATTGATTTCTATGCCAGATTTGTCGTCCCACTTGCCTTTCTCGCTTTCAA
TGTTATCTACTGGGTATCATGTCTTATCATGTCTGCCAATGCTTCCACTCC
AGAGTCTCTCGTTTAGATTTTCCCCTGTTTTTTTTTCAAATCCCCACTGTTC
CCACATTTGCTATCAATTTGCAAACATCATACTTGATACCGGTATATGTAA
ATGAAATTTGAAATTTAAAATTTAAATAAAAAATAAAAAATAAAACTCA
CTTGCAAAAAAAAAAAAAAAAAAAAA
```

FIG.2

TPQYCINWQLYIFASAMATWIVGKLIIASLILGIQAQQARTKSQDIFEDDNDNG
TTTLESLARLTSPIHIPIEQPQTSDSKILAHLFTSGYDFRVRPPTDNGGPVVVSVN
MLLRTISKIDVVNMEYSAQLTLRESWIDKRLSYGVKGDGQPDFVILTVGHQIW
MPDTFFPNEKQAYKHTIDKPNVLIRIHNDGTVLYSVRISLVLSCPMYLQYYPM
DVQQCSIDLASYAYTTKDIEYLWKEHSPLQLKVGLSSSLPSFQLTNTSTTYCTSV
TNTGIYSCLRTTIQLKREFSFYLLQLYIPSCMLVIVSWVSFWFDRTAIPARVTLGV
TTLLTMTAQSAGINSQLPPVSYIKAIDVWIGACMTFIFCALLEFALVNHIANKQ
GVERKARTEREKAEIPLLQNLHNDVPTKVFNQEEKVRTVPLNRRQMNSFLNL
LETKTEWNDISKRVDLISRALFPVLFFVFNILYWSRFGQQNVLF*ICKSNKFLFY
GKNDRECF*FNLNETV*KIKKKKKK

FIG.3

NNAIMTTPSSFSILLLLLLMPVVTNGEYSMQSEQEILNALLKNYDMRVRPPPA
NSSTEGAVNVRVNIMIRMLSKIDVVNMEYSIQLTFREQWIDPRLAYENLGFYN
PPAFLTVPHVKKSLWIPDTFFPTEKAAHRHLIDMENMFLRIYPDGKILYSSRISL
TSSCPMRLQLYPLDYQSCNFDLVSYAHTMNDIMYEWDPSTPVQLKPGVGSDL
PNFILKNYTTNADCTSHTNTGSYGCLRMQLLFKRQFSYYLVQLYAPTTMIVIVS
WVSFWIDLHSTAGRVALGVTTLLTMTTMQSAINAKLPPVSYVKVVDVWLGA
CQTFVFGALLEYAFVSYQDSVRQNDRSREKAARKAQRRREKLEMVDAEVYQP
PCTCHTFEARETFRDKVRRYFTKPDYLPAKIDFYARFVVPLAFLAFNVIYWVSC
LIMSANASTPESLV*IFPCFFFKSPLFPHLLSICKHHT*YRYM*MKFEI*NLNKK*KI
KLTCKKKKKK

FIG.4

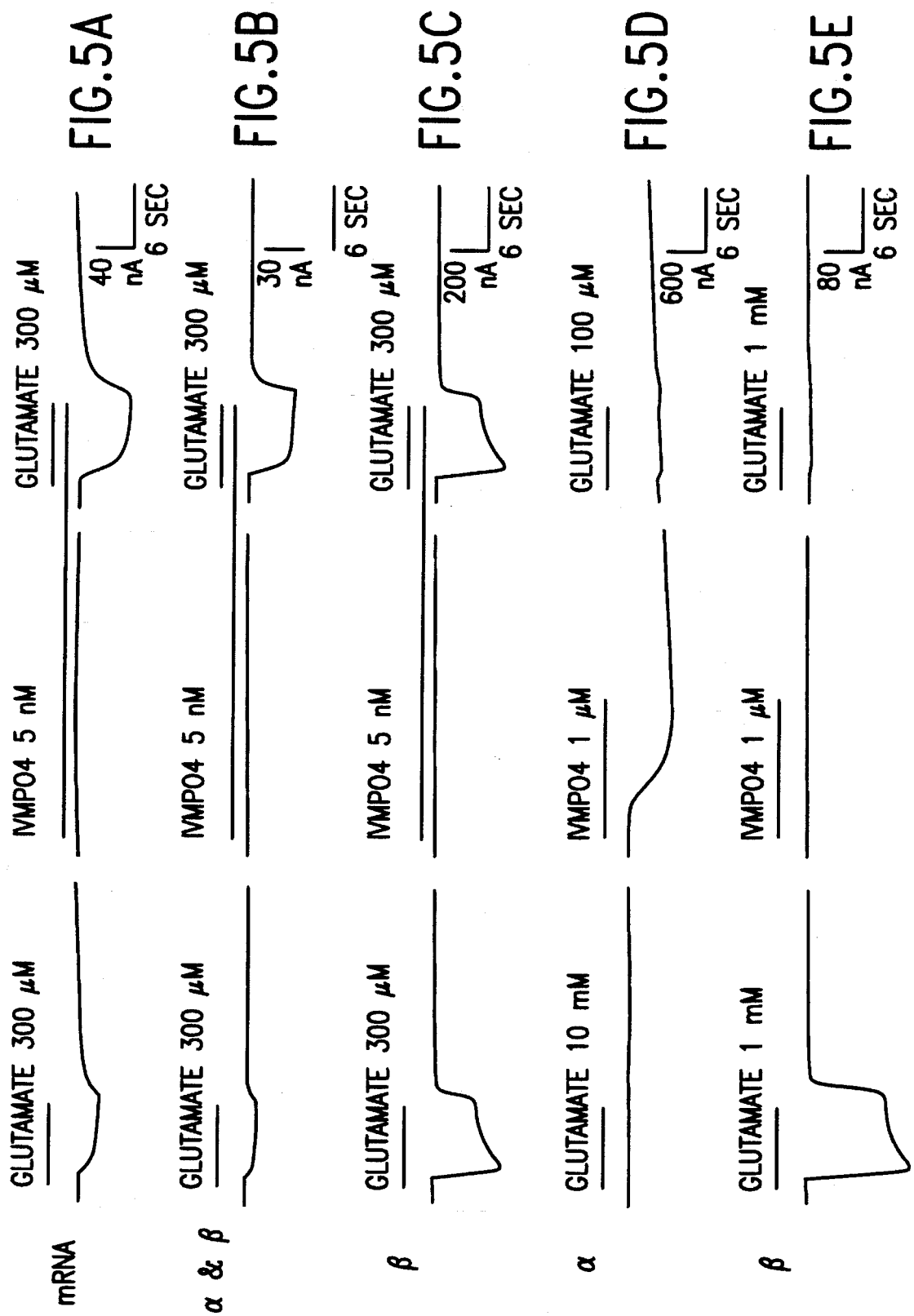

| INJECTION | | $E_{REV}$ (mV) | | | |
|---|---|---|---|---|---|
| POLY (A)$^+$ RNA | LIGAND | NaCl | KCl | CholineCl | Na ISETHIONATE |
| α & β | IVMPO$_4$ | −33 ± 2 | −33 ± 2 | −30 ± 3 | 38 ± 6 |
| α & β | IVMPO$_4$ | −34 ± 1 | −34 ± 1 | −31 ± 1 | 29 ± 3 |
| α & β | GLUTAMATE | −30 ± 1 | −28 ± 1 | −27 ± 1 | 27 ± 3 |
| α | IVMPO$_4$ | −34 ± 1 | −34 ± 1 | −32 ± 2 | 2 ± 1 |
| β | GLUTAMATE | −34 ± 3 | −35 ± 3 | −32 ± 2 | 34 ± 3 |

FIG.6A

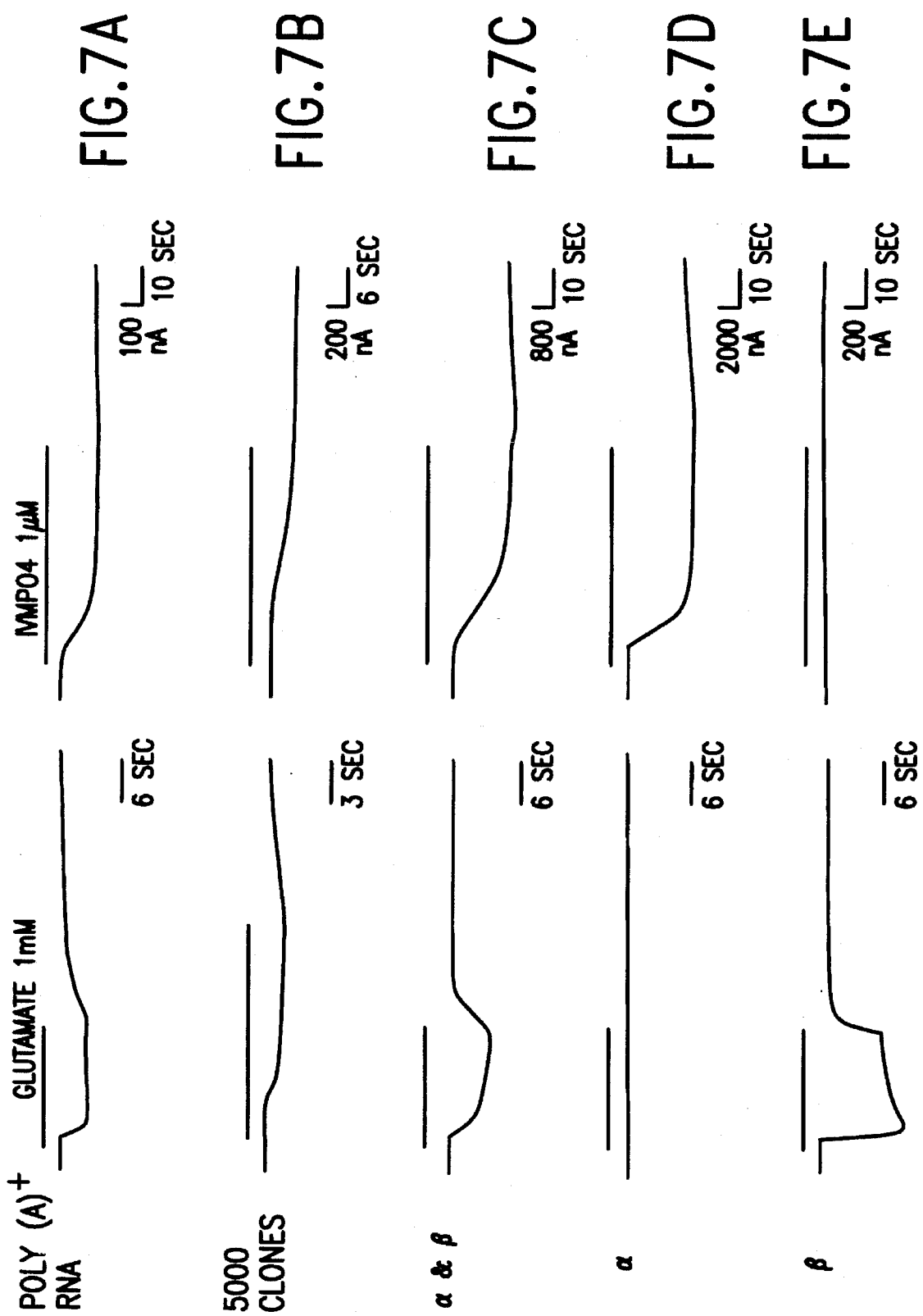

5,527,703

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 1542 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| TAACCCCTCA | ATACTGCATA | AATTGGCAAT | TATATATTTT | TGCTTCGGCA | ATGGCTACCT | 60 |
| GGATTGTCGG | AAAGCTGATC | ATTGCATCTT | TAATTTTGGG | AATACAAGCC | CAACAAGCTA | 120 |
| GAACGAAATC | ACAAGATATT | TTCGAAGATG | ATAATGATAA | TGGAACGACT | ACACTGGAAT | 180 |
| CGCTAGCCAG | ATTAACATCC | CCGATTCACA | TTCCAATTGA | ACAACCTCAA | ACATCGGACT | 240 |
| CAAAAATTCT | AGCTCATCTT | TTCACATCTG | GATACGATTT | CCGAGTGCGA | CCTCCAACAG | 300 |
| ATAATGGAGG | ACCAGTTGTG | GTTTCAGTTA | ACATGCTCCT | TCGAACTATT | TCAAAGATAG | 360 |
| ATGTTGTGAA | TATGGAGTAT | AGTGCTCAAT | TGACATTGCG | AGAGAGTTGG | ATTGACAAGA | 420 |
| GACTCAGCTA | CGGAGTAAAA | GGAGATGGTC | AGCCAGATTT | TGTGATTCTC | ACTGTTGGAC | 480 |
| ATCAAATTTG | GATGCCCGAC | ACGTTTTCC | CGAATGAGAA | ACAAGCTTAC | AAGCATACGA | 540 |
| TTGATAAGCC | GAATGTATTG | ATTCGAATAC | ACAATGATGG | TACAGTATTG | TACTCTGTTC | 600 |
| GTATTTCACT | AGTCCTCTCT | TGCCCAATGT | ATCTACAGTA | CTATCCAATG | GATGTTCAAC | 660 |
| AGTGTTCCAT | TGATCTTGCA | TCGTATGCCT | ACACTACAAA | AGATATCGAA | TATTTGTGGA | 720 |
| AAGAGCATTC | ACCACTTCAG | TTAAAGGTTG | GATTATCAAG | CTCGTTGCCT | TCATTCCAGT | 780 |
| TGACTAATAC | TTCAACGACA | TATTGCACCA | GTGTAACAAA | CACTGGCATT | TATTCCTGTT | 840 |
| TGCGAACTAC | TATTCAGTTA | AAGAGAGAGT | TCAGTTTTTA | CCTTCTCCAA | CTCTACATCC | 900 |
| CGTCATGCAT | GCTAGTCATC | GTATCCTGGG | TTTCATTTTG | GTTTGATCGA | ACTGCAATCC | 960 |
| CGGCTCGTGT | CACCCTCGGA | GTCACCACGC | TGCTTACAAT | GACAGCTCAA | TCAGCCGGTA | 1020 |
| TCAATTCACA | ACTACCTCCA | GTTTCCTATA | TCAAGGCGAT | TGATGTCTGG | ATTGGTGCAT | 1080 |
| GTATGACATT | CATTTTCTGC | GCGTTGTTGG | AGTTTGCATT | GGTAAATCAT | ATAGCTAACA | 1140 |
| AGCAGGGTGT | TGAGAGAAAA | GCTCGAACTG | AAAGAGAGAA | AGCTGAAATT | CCACTTCTTC | 1200 |
| AAAATTTGCA | CAATGATGTT | CCCACAAAGG | TTTTCAATCA | AGAGGAAAAA | GTAAGGACAG | 1260 |
| TTCCACTGAA | TCGCCGGCAA | ATGAATAGCT | TCTTGAATTT | GCTCGAGACA | AAAACCGAAT | 1320 |
| GGAATGACAT | ATCAAAACGA | GTCGATCTTA | TTTCTCGAGC | CCTGTTTCCT | GTTCTATTTT | 1380 |
| TTGTTTTTAA | CATTTTGTAC | TGGTCTCGTT | TTGGCCAGCA | GAACGTATTA | TTTTAGATTT | 1440 |

| GTAAATCGAA | TAAGTTTTTG | TTTTATGGCA | AAAATGATCG | AGAATGCTTT | TGATTTAATC | 1500 |
| GAATGAAAC | TGTTTAAAAA | ATTAAAAAAA | AAAAAAAAAA | AA | | 1542 |

(2) INFORMATION FOR SEQ ID NO:2:

(i) SEQUENCE CHARACTERISTICS:
        (A) LENGTH: 1479 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| CAATAATGCA | ATTATGACTA | CACCTAGTTC | ATTTTCAATT | CTGCTCCTCC | TGCTACTGAT | 60 |
| GCCCGTCGTC | ACAAATGGCG | AGTACAGTAT | GCAATCGGAG | CAGGAGATTC | TCAATGCGTT | 120 |
| GCTCAAAAAT | TATGACATGC | GGGTACGGCC | ACCACCGGCC | AACTCATCAA | CGGAAGGTGC | 180 |
| TGTCAATGTT | CGTGTTAATA | TTATGATTCG | GATGCTATCG | AAAATTGATG | TAGTTAATAT | 240 |
| GGAATATTCA | ATTCAACTAA | CATTCCGCGA | GCAATGGATA | GATCCTCGAC | TGGCCTATGA | 300 |
| AAATTTGGGT | TTCTACAATC | CTCCGGCATT | TCTCACAGTC | CCACATGTTA | AAAAGAGTCT | 360 |
| ATGGATTCCT | GACACATTCT | TTCCCACCGA | AAAAGCAGCT | CATAGACATT | TGATTGATAT | 420 |
| GGAAAACATG | TTCTTGAGGA | TATATCCGGA | TGGAAAAATC | CTCTACAGTT | CCCGGATAAG | 480 |
| TTTGACAAGT | TCCTGCCCAA | TGCGTCTCCA | ACTCTACCCA | CTCGACTATC | AATCGTGTAA | 540 |
| CTTTGATCTT | GTCAGCTACG | CGCACACAAT | GAATGATATC | ATGTACGAGT | GGGATCCATC | 600 |
| AACACCAGTT | CAACTGAAAC | CCGGCGTTGG | CTCGGATCTT | CCCAATTTTA | TACTCAAAAA | 660 |
| CTACACAACA | AATGCAGATT | GCACAAGCCA | CACGAACACA | GGATCATATG | GATGTCTCCG | 720 |
| AATGCAACTT | TTGTTCAAAC | GGCAATTCAG | TTATTACTTG | GTACAACTGT | ATGCTCCAAC | 780 |
| CACTATGATT | GTGATTGTCT | CATGGGTTTC | ATTTTGGATT | GATCTTCATT | CAACTGCTGG | 840 |
| ACGTGTCGCT | TTAGGAGTCA | CTACGCTTCT | TACAATGACT | ACAATGCAAT | CTGCAATCAA | 900 |
| CGCCAAGCTT | CCACCAGTTA | GCTACGTAAA | AGTTGTGGAT | GTCTGGCTTG | GAGCGTGCCA | 960 |
| AACATTTGTA | TTCGGAGCAC | TTCTGGAATA | CGCATTTGTC | AGTTATCAAG | ATAGTGTCCG | 1020 |
| GCAAAATGAC | AGGTCAAGAG | AGAAAGCTGC | AAGGAAGGCG | CAGAGAAGGA | GAGAAAAGTT | 1080 |
| GGAAATGGTG | GATGCAGAAG | TCTATCAGCC | ACCGTGCACC | TGTCATACTT | TCGAAGCCCG | 1140 |
| CGAGACATTC | CGTGACAAAG | TCCGCCGTTA | CTTCACAAAA | CCAGATTATC | TACCGGCAAA | 1200 |
| AATTGATTTC | TATGCCAGAT | TTGTCGTCCC | ACTTGCCTTT | CTCGCTTTCA | ATGTTATCTA | 1260 |
| CTGGGTATCA | TGTCTTATCA | TGTCTGCCAA | TGCTTCCACT | CCAGAGTCTC | TCGTTTAGAT | 1320 |
| TTTCCCCTGT | TTTTTTTTCA | AATCCCCACT | GTTCCCACAT | TTGCTATCAA | TTTGCAAACA | 1380 |
| TCATACTTGA | TACCGGTATA | TGTAAATGAA | ATTTGAAATT | TAAAATTTAA | ATAAAAAATA | 1440 |
| AAAAATAAAA | CTCACTTGCA | AAAAAAAAA | AAAAAAAA | | | 1479 |

(2) INFORMATION FOR SEQ ID NO:3:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Thr  Pro  Gln  Tyr  Cys  Ile  Asn  Trp  Gln  Leu  Tyr  Ile  Phe  Ala  Ser  Ala
  1              5                        10                       15
Met  Ala  Thr  Trp  Ile  Val  Gly  Lys  Leu  Ile  Ile  Ala  Ser  Leu  Ile  Leu
               20                        25                       30
Gly  Ile  Gln  Ala  Gln  Ala  Arg  Thr  Lys  Ser  Gln  Asp  Ile  Phe  Glu
          35                        40                       45
Asp  Asp  Asn  Asp  Asn  Gly  Thr  Thr  Leu  Glu  Ser  Leu  Ala  Arg  Leu
 50                        55                       60
Thr  Ser  Pro  Ile  His  Ile  Pro  Ile  Glu  Gln  Pro  Gln  Thr  Ser  Asp  Ser
 65                        70                       75                       80
Lys  Ile  Leu  Ala  His  Leu  Phe  Thr  Ser  Gly  Tyr  Asp  Phe  Arg  Val  Arg
               85                        90                       95
Pro  Pro  Thr  Asp  Asn  Gly  Gly  Pro  Val  Val  Ser  Val  Asn  Met  Leu
               100                       105                      110
Leu  Arg  Thr  Ile  Ser  Lys  Ile  Asp  Val  Val  Asn  Met  Glu  Tyr  Ser  Ala
               115                       120                      125
Gln  Leu  Thr  Leu  Arg  Glu  Ser  Trp  Ile  Asp  Lys  Arg  Leu  Ser  Tyr  Gly
          130                       135                      140
Val  Lys  Gly  Asp  Gly  Gln  Pro  Asp  Phe  Val  Ile  Leu  Thr  Val  Gly  His
145                       150                       155                      160
Gln  Ile  Trp  Met  Pro  Asp  Thr  Phe  Phe  Pro  Asn  Glu  Lys  Gln  Ala  Tyr
               165                       170                      175
Lys  His  Thr  Ile  Asp  Lys  Pro  Asn  Val  Leu  Ile  Arg  Ile  His  Asn  Asp
               180                       185                      190
Gly  Thr  Val  Leu  Tyr  Ser  Val  Arg  Ile  Ser  Leu  Val  Leu  Ser  Cys  Pro
               195                       200                      205
Met  Tyr  Leu  Gln  Tyr  Tyr  Pro  Met  Asp  Val  Gln  Gln  Cys  Ser  Ile  Asp
     210                       215                      220
Leu  Ala  Ser  Tyr  Ala  Tyr  Thr  Thr  Lys  Asp  Ile  Glu  Tyr  Leu  Trp  Lys
225                       230                       235                      240
Glu  His  Ser  Pro  Leu  Gln  Leu  Lys  Val  Gly  Leu  Ser  Ser  Ser  Leu  Pro
               245                       250                      255
Ser  Phe  Gln  Leu  Thr  Asn  Thr  Ser  Thr  Thr  Tyr  Cys  Thr  Ser  Val  Thr
               260                       265                      270
Asn  Thr  Gly  Ile  Tyr  Ser  Cys  Leu  Arg  Thr  Thr  Ile  Gln  Leu  Lys  Arg
               275                       280                      285
Glu  Phe  Ser  Phe  Tyr  Leu  Leu  Gln  Leu  Tyr  Ile  Pro  Ser  Cys  Met  Leu
     290                       295                      300
Val  Ile  Val  Ser  Trp  Val  Ser  Phe  Trp  Phe  Asp  Arg  Thr  Ala  Ile  Pro
305                       310                       315                      320
Ala  Arg  Val  Thr  Leu  Gly  Val  Thr  Thr  Leu  Leu  Thr  Met  Thr  Ala  Gln
               325                       330                      335
Ser  Ala  Gly  Ile  Asn  Ser  Gln  Leu  Pro  Pro  Val  Ser  Tyr  Ile  Lys  Ala
               340                       345                      350
Ile  Asp  Val  Trp  Ile  Gly  Ala  Cys  Met  Thr  Phe  Ile  Phe  Cys  Ala  Leu
               355                       360                      365
Leu  Glu  Phe  Ala  Leu  Val  Asn  His  Ile  Ala  Asn  Lys  Gln  Gly  Val  Glu
     370                       375                      380
Arg  Lys  Ala  Arg  Thr  Glu  Arg  Glu  Lys  Ala  Glu  Ile  Pro  Leu  Leu  Gln
385                       390                       395                      400
Asn  Leu  His  Asn  Asp  Val  Pro  Thr  Lys  Val  Phe  Asn  Gln  Glu  Glu  Lys
               405                       410                      415
Val  Arg  Thr  Val  Pro  Leu  Asn  Arg  Arg  Gln  Met  Asn  Ser  Phe  Leu  Asn
```

|   |   |   | 420 |   |   |   |   | 425 |   |   |   |   | 430 |   |   |
|---|---|---|---|---|---|---|---|---|---|---|---|---|---|---|---|

Leu Leu Glu Thr Lys Thr Glu Trp Asn Asp Ile Ser Lys Arg Val Asp
            435                 440             445

Leu Ile Ser Arg Ala Leu Phe Pro Val Leu Phe Phe Val Phe Asn Ile
        450             455             460

Leu Tyr Trp Ser Arg Phe Gly Gln Gln Asn Val Leu Phe Ile Cys Lys
465             470             475                         480

Ser Asn Lys Phe Leu Phe Tyr Gly Lys Asn Asp Arg Glu Cys Phe Phe
            485             490                 495

Asn Leu Asn Glu Thr Val Lys Ile Lys Lys Lys Lys Lys
            500             505             510

(2) INFORMATION FOR SEQ ID NO:4:

(i) SEQUENCE CHARACTERISTICS:
        (A) LENGTH: 487 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Asn Asn Ala Ile Met Thr Thr Pro Ser Ser Phe Ser Ile Leu Leu Leu
1               5               10                      15

Leu Leu Leu Met Pro Val Val Thr Asn Gly Glu Tyr Ser Met Gln Ser
            20              25              30

Glu Gln Glu Ile Leu Asn Ala Leu Leu Lys Asn Tyr Asp Met Arg Val
        35              40              45

Arg Pro Pro Pro Ala Asn Ser Ser Thr Glu Gly Ala Val Asn Val Arg
        50              55              60

Val Asn Ile Met Ile Arg Met Leu Ser Lys Ile Asp Val Val Asn Met
65              70              75                      80

Glu Tyr Ser Ile Gln Leu Thr Phe Arg Glu Gln Trp Ile Asp Pro Arg
            85              90                      95

Leu Ala Tyr Glu Asn Leu Gly Phe Tyr Asn Pro Pro Ala Phe Leu Thr
            100             105             110

Val Pro His Val Lys Lys Ser Leu Trp Ile Pro Asp Thr Phe Phe Pro
            115             120             125

Thr Glu Lys Ala Ala His Arg His Leu Ile Asp Met Glu Asn Met Phe
        130             135             140

Leu Arg Ile Tyr Pro Asp Gly Lys Ile Leu Tyr Ser Ser Arg Ile Ser
145             150             155             160

Leu Thr Ser Ser Cys Pro Met Arg Leu Gln Leu Tyr Pro Leu Asp Tyr
                165             170             175

Gln Ser Cys Asn Phe Asp Leu Val Ser Tyr Ala His Thr Met Asn Asp
            180             185             190

Ile Met Tyr Glu Trp Asp Pro Ser Thr Pro Val Gln Leu Lys Pro Gly
        195             200             205

Val Gly Ser Asp Leu Pro Asn Phe Ile Leu Lys Asn Tyr Thr Thr Asn
    210             215             220

Ala Asp Cys Thr Ser His Thr Asn Thr Gly Ser Tyr Gly Cys Leu Arg
225             230             235             240

Met Gln Leu Leu Phe Lys Arg Gln Phe Ser Tyr Tyr Leu Val Gln Leu
            245             250             255

Tyr Ala Pro Thr Thr Met Ile Val Ile Val Ser Trp Val Ser Phe Trp
            260             265             270

| | | | | | | | | | | | | | | | |
|---|---|---|---|---|---|---|---|---|---|---|---|---|---|---|---|
| Ile | Asp | Leu 275 | His | Ser | Thr | Ala | Gly 280 | Arg | Val | Ala | Leu | Gly 285 | Val | Thr | Thr |
| Leu | Leu 290 | Thr | Met | Thr | Thr | Met 295 | Gln | Ser | Ala | Ile | Asn 300 | Ala | Lys | Leu | Pro |
| Pro 305 | Val | Ser | Tyr | Val | Lys 310 | Val | Val | Asp | Val | Trp 315 | Leu | Gly | Ala | Cys | Gln 320 |
| Thr | Phe | Val | Phe | Gly 325 | Ala | Leu | Leu | Glu | Tyr 330 | Ala | Phe | Val | Ser | Tyr 335 | Gln |
| Asp | Ser | Val | Arg 340 | Gln | Asn | Asp | Arg | Ser 345 | Arg | Glu | Lys | Ala | Ala 350 | Arg | Lys |
| Ala | Gln | Arg 355 | Arg | Arg | Glu | Lys | Leu 360 | Glu | Met | Val | Asp | Ala 365 | Glu | Val | Tyr |
| Gln | Pro 370 | Pro | Cys | Thr | Cys | His 375 | Thr | Phe | Glu | Ala | Arg 380 | Glu | Thr | Phe | Arg |
| Asp 385 | Lys | Val | Arg | Arg | Tyr 390 | Phe | Thr | Lys | Pro | Asp 395 | Tyr | Leu | Pro | Ala | Lys 400 |
| Ile | Asp | Phe | Tyr | Ala 405 | Arg | Phe | Val | Val | Pro 410 | Leu | Ala | Phe | Leu | Ala 415 | Phe |
| Asn | Val | Ile | Tyr 420 | Trp | Val | Ser | Cys | Leu 425 | Ile | Met | Ser | Ala | Asn 430 | Ala | Ser |
| Thr | Pro | Glu 435 | Ser | Leu | Val | Ile | Phe 440 | Pro | Cys | Phe | Phe | Phe 445 | Lys | Ser | Pro |
| Leu | Phe 450 | Pro | His | Leu | Leu | Ser 455 | Ile | Cys | Lys | His | His 460 | Thr | Tyr | Arg | Tyr |
| Met 465 | Met | Lys | Phe | Glu | Ile 470 | Asn | Leu | Asn | Lys | Lys 475 | Lys | Ile | Lys | Leu | Thr 480 |
| Cys | Lys | Lys | Lys | Lys 485 | Lys | Lys | | | | | | | | | |

( 2 ) INFORMATION FOR SEQ ID NO:5:

( i ) SEQUENCE CHARACTERISTICS:
       ( A ) LENGTH: 46 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:5:

GAGAGAGAGA GAGAGAGAGA GCGGCCGCTT TTTTTTTTTT TTTTTT    46

DNA ENCODING GLUTAMATE GATED CHLORIDE CHANNELS

BACKGROUND OF THE INVENTION

The avermectins are a family of macrocyclic lactones originally isolated from the actinomycete *Streptomyces avermitilis*. The semisynthetic avermectin derivative, ivermectin (22,23-dihydroavermectin $B_{1a}$), is used throughout the world to treat parasitic helminths and insect pests of man and animals. Discovered some 15 years ago, the avermectins remain the most potent broad spectrum endectocides exhibiting low toxicity to the host. Avermectins exhibit an essentially irreversible interaction with a high affinity site in nematode [Schaeffer, J. M. & Haines, H. W. *Biochem. Pharm.* 38, 2329–2338 (1989); Cully, D. F. & Paress P. S., *Molecular Pharm.* 40:326–332 (1991)] and insect [Rohrer, S. P., Meinke, P. T., Hayes, E. C., Mrozik, H. & Schaeffer, J. M. *Proc. Natl. Acad. Sci,* 89, 4168–4172 (1992)] membranes and induce an increase in membrane chloride permeability in nematodes [Martin, R. J. & Pennington, A. J. *Br. J. Pharmacol.* 98, 747–756 (1989)], arthropods [Scott, R. H. & Duce, I. R. *Pestic. Sci.* 16, 599–604 (1985)], [Duce, I. R. & Scott, R. H. *Brit. J. Pharmacol.* 85, 395–401 (1985)] and crustaceans [Zufall, F., Franke, C. & Hatt, H. *J. Exp. Biol.* 142, 191–205 (1989)]. The natural ligand of the avermectin-sensitive chloride channel remains unclear [Turner, M. J. & Schaeffer, J. M. *Ivermectin and Abamectin* (eds. Campbell, W. C.) 73–88 (Springer-Verlag, New York, 1989)]. Glutamate-gated chloride channels, or H-receptors, have been identified in arthropod nerve and muscle [Lingle, C. & Marder, E. *Brain Res.* 212, 481–488 (1981)], [Horseman, B. G., Seymour, C., Bermudez, I. & Beadle, D. J. *Neurosci. Lett.* 85, 65–70 (1988)], [Wafford, K. A. & Sattelle, D. B. *J. Exp. Bio.* 144, 449–462 (1989)], [Lea, T. J. & Usherwood, P. N. R. *Comp. Gen. Parmacol.* 4, 333–350 (1973)], [Cull-Candy, S. G. *J. Physiol.* 255, 449–464 (1976)]. It has been proposed that avermectins activate glutamate-gated chloride channels on locust muscle [Scott, R. H. & Duce, I. R. *Pestle, Sci.* 16, 599–604 (1985)].

The soil nematode *Caenorhabditis elegans* is very sensitive to the avermectins and is used as an in vitro model to examine the efficacy of different anthelminthic compounds [Schaeffer, J. M. & Haines, H. W. *Biochem. Pharm.* 38, 2329–2338 (1989)]. *Xenopus laevis* oocytes injected with *C. elegans* poly $(A)^+$ RNA express an avermectin-sensitive chloride channel [Arena, J. P., Liu, K. K., Paress, P. S. & Cully, D. F. *Mol. Pharmacol.* 40, 368–374 (1991 )]. It has been established that this channel is also sensitive to glutamate [Arena, J. P., Liu, K. K., Paress, P. S., Schaeffer, J. M. & Cully, D. F. *Mol. Brain Res.* 15, 339–348 (1992)]. Similar to the H-receptors from locust muscle, the glutamate- and avermectin-sensitive current is activated by ibotenate and blocked with low affinity by picrotoxin [Scott, R. H. & Duce, I. R. *Pestic, Sci.* 16, 599–604 (1985)], [Lea, T. J. & Usherwood, P. N. R. *Comp. Gen. Pharmacol.* 4, 333–350 (1973)], [Cull-Candy, S. G. *J. Physiol.* 255, 449–464 (1976)], [Arena, J. P., Liu, K. K., Paress, P. S., Schaeffer, J. M. & Cully, D. F. *Mol. Brain Res.* 15, 339–348 (1992)].

SUMMARY OF THE INVENTION

A target of avermectin action in invertebrates has been cloned and characterized and it represents a novel class of ligand-gated chloride channels. Using a recombinant expression system two functional DNA molecules encoding the invertebrate glutamate- and avermectin-sensitive chloride channels have been isolated. The electrophysiological and structural properties of these proteins are disclosed, as is the amino acid and nucleotide sequence. The recombinant protein is useful to identify modulators of the channel. Modulators identified in this process are useful as therapeutic agents, insecticides and anthelminthics.

BRIEF DESCRIPTION OF THE DRAWINGS

FIG. 1 - The nucleotide sequence of GluClα is shown.

FIG. 2 - The nucleotide sequence of GluClβ is shown.

FIG. 3 - The amino acid sequence of GluClα is shown.

FIG. 4 - The amino acid sequence of GluClβ is shown

FIGS. 5A, 5B, 5C, 5D, 5E - Electrophysiological properties of glutamate- and IVMPO$_4$-sensitive currents in Xenopus oocytes.

FIGS. 7A, 7B, 7C, 7D, 7E, 7F, 7G - Modulation of glutamate-sensitive current by IVMPO$_4$ FIG. 8 - A phylogenetic analysis of GluClα and GluClβ is shown.

DETAILED DESCRIPTION

Figure 6B:
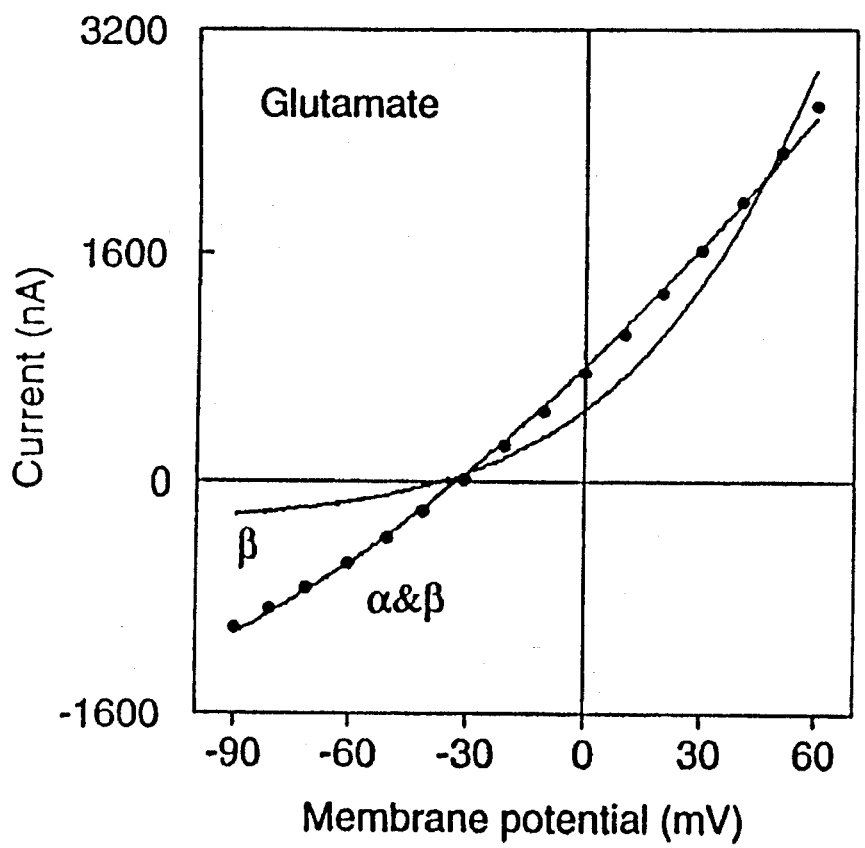
FIGS. 6A, B, and C - Permeability and voltage-dependence of GluClα and GluClβ.

The present invention relates to DNA encoding invertebrate glutamate- and avermectin-sensitive chloride channels (GluCl) which were isolated from GluCl producing cells. GluCl, as used herein, refers to protein which can specifically function as an anion channel gated by glutamate.

The amino acid sequence of invertebrate GluCl was not previously known, nor was the nucleotide sequence encoding GluCl known. This is the first reported cloning of a glutamate-gated chloride channel. It is also the first report of the cloning of an invertebrate target of avermectin and an invertebrate avermectin-sensitive chloride channel. It is predicted that all organisms sensitive to the avermectins will contain the described glutamate and avermectin-sensitive channels. Invertebrate cells capable of producing GluCl include, but are not limited to muscle or nerve cells isolated from organisms that show sensitivity to the avermectins. Avermectin sensitive animals are diverse and include invertebrates belonging to the phyla Arthropoda and Nematoda.

Other cells and cell lines may also be suitable for use to isolate GluCl cDNA. Selection of suitable cells may be done by screening for GluCl activity in cell extracts. GluCl activity can be monitored by performing a $^3$H-ivermectin binding assay (Cully and Paress, supra; Rohrer et al, supra) or by direct electrophysiological measurment of a glutamate and avermectin-sensitive chloride channel [Martin, R. J. & Pennington, A. J. *Br. J. Pharmacol.* 98, 747–756 (1989); Scott, R. H. & Duce, I. R. *Pestic. Sci.* 16, 599–604 (1985); Duce, I. R. & Scott, R. H. *Brit. J. Pharmacol.* 85, 395–401 (1985); Zufall, F., Franke, C. & Hatt, H. *J. Exp. Biol.* 142, 191–205 (1989)]. Cells which possess GluCl activity in this assay may be suitable for the isolation of GluCl DNA or mRNA.

Any of a variety of procedures known in the art may be used to molecularly clone GluCl DNA. These methods include, but are not limited to, direct functional expression of the GluCl genes following the construction of a GluCl-containing cDNA library in an appropriate expression vector system. Another method is to screen GluCl-containing cDNA library constructed in a bacteriophage or plasmid shuttle vector with a labelled oligonucleotide probe designed from the amino acid sequence of the GluCl subunits. An additional method consists of screening a GluCl-containing cDNA library constructed in a bacteriophage or plasmid shuttle vector with a partial cDNA encoding the GluCl subunits. This partial cDNA is obtained by the specific PCR amplification of GluCl DNA fragments through the design of degenerate oligonucleotide primers from the amino acid sequence of the purified GluCl subunits.

Another method is to isolate RNA from GluCl-producing cells and translate the RNA into protein via an in vitro or an in vivo translation system. The translation of the RNA into a peptide a protein will result in the production of at least a portion of the GluCl protein which an be identified by, for example, immunological reactivity with an anti-GluCl antibody or by biological activity of GluCl protein. In this method, pools of RNA isolated from GluCl-producing cells can be analyzed for the presence of an RNA which encodes at least a portion of the GluCl protein. Further fractionation of the RNA pool can be done to purify the GluCl RNA from non-GluCl RNA. The peptide or protein produced by this method may be analyzed to provide amino acid sequences which in turn are used to provide primers for production of GluCl cDNA, or the RNA used for translation can be analyzed to provide nucleotide sequences encoding GluCl and produce probes for this production of GluCl cDNA. This method is known in the art and can be found in, for example, Maniatis, T., Fritsch, E. F., Sambrook, J. in Molecular Cloning: A Laboratory Manual, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating GluCl-encoding DNA. Other types of libraries include, but are not limited to, cDNA libraries derived from other cells, from organisms other than *C. elegans,* and genomic DNA libraries that include YAC (yeast artificial chromosome) and cosmid libraries.

It is readily apparent to those skilled in the art that suitable cDNA libraries may be prepared from cells or cell lines which have GluCl activity. The selection of cells or cell lines for use in preparing a cDNA library to isolate GluCl cDNA may be done by first measuring cell associated GluCl activity using the electrophysiological measurment of avermectin and glutamate-sensitive chloride channels or a glutamate or avermectin ligand binding assay.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding GluCl may also be isolated from a suitable genomic DNA library. Construction of genomic DNA libraries can be performed by standard techniques well known in the art. Well known genomic DNA library construction techiques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

In order to clone the GluCl gene by the above methods, the amino acid sequence of GluCl may be necessary. To accomplish this, GluCl protein may be purified and partial amino acid sequence determined by automated sequenators. It is not necessary to determine the entire amino acid sequence, but the linear sequence of two regions of 6 to 8 amino acids from the protein is determined for the production of primers for PCR amplification of a partial GluCl DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the GluCl sequence but will be capable of hybridizing to GluCl DNA even in the presence of DNA oligonucleotides with mismatches. The mismatched DNA oligonucleotides may still sufficiently hybridize to the GluCl DNA to permit identification and isolation of GluCl encoding DNA. DNA isolated by these methods can be used to screen DNA libraries from a variety of cell types, from invertebrate and vertebrate sources, and to isolate homologous genes.

Purified biologically active GluCl may have several different physical forms. GluCl may exist as a full-length nascent or unprocessed polypeptide, or as partially processed polypeptides or combinations of processed polypeptides. The full-length nascent GluCl polypeptide may be postranslationally modified by specific proteolytic cleavage events which result in the formation of fragments of the full length nascent polypeptide. A fragment, or physical association of fragments may have the full biological activity associated with GluCl (glutamate gated and avermectin gated chloride channel) however, the degree of GluCl activity may vary between individual GluCl fragments and physically associated GluCl polypeptide fragments.

The cloned GluCl DNA obtained through the methods described herein may be recombinantly expressed by molecular cloning into an expression vector containing a suitable promoter and other appropriate transcription regulatory elements, and transferred into prokaryotic or eukaryotic host cells to produce recombinant GluCl. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli,* bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant GluCl in mammalian cells. Commercially available mammalian expression vectors which may be suitable for recombinant GluCl expression, include but are not limited to, pMAMneo (Clontech), pcDNA3

(Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express recombinant GluCl in bacterial cells. Commercially available bacterial expression vectors which may be suitable for recombinant GluCl expression include, but are not limited to pET vectors (Novagen) and pQE vectors (Qiagen).

A variety of fungal cell expression vectors may be used to express recombinant GluCl in fungal cells such as yeast. Commerically available fungal cell expression vectors which may be suitable for recombinant GluCl expression include but are not limited to pYES2 (Invitrogen) and Pichia expression vector (Invitrogen).

A variety of insect cell expression vectors may be used to express recombinant GluCl in insect cells. Commercially available insect cell expression vectors which may be suitable for recombinant expression of GluCl include but are not limited to pBlueBacII (Invitrogen).

DNA encoding GluCl may also be cloned into an expression vector for expression in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to drosophila and silkworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce GluCl protein. Identification of GluCl expressing host cell clones may be done by several means, including but not limited to immunological reactivity with anti-GluCl antibodies, and the presence of host cell-associated GluCl activity.

Expression of GluCl DNA may also be performed using in vitro produced synthetic mRNA. Synthetic mRNA or mRNA isolated from GluCl producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the GluCl DNA sequence(s) that yields optional levels of GluCl activity and/or GluCl protein, GluCl DNA molecules including, but not limited to, the following can be constructed: the full-length open reading frame of the GluCl cDNA encoding the GluClα (52,550 kDa) and GluClβ (49,900kDa) subunits is from approximately base 51 to approximately base 1433 and from approximately base 14 to approximately base 1315, respectively, (these numers correspond to first nucleotide of first methionine and last nucleotide before the first stop codon) and several constructs containing portions of the cDNA encoding GluCl protein. All constructs can be designed to contain none, all or portions of the 5' or the 3' untranslated region of GluCl cDNA. GluCl activity and levels of protein expression can be determined following the introduction, both singly and in combination, of these constructs into appropriate host cells. Following determination of the GluCl DNA cassette yielding optimal expression in transient assays, this GluCl DNA construct is transferred to a variety of expression vectors, for expression in host cells including, but not limited to, mammalian cells, baculovirus-infected insect cells, E. coli, and the yeast S. cerevisiae.

Host cell transfectants and microinjected oocytes may be assayed for both the levels of GluCl channel activity and levels of GluCl protein by the following methods. In the case of recombinant host cells, this involves the co-transfection of one or possibly two or more plasmids, containing the GluCl DNA encoding one or more subunits. In the case of oocytes, this involves the co-injection of synthetic RNAs for one or more GluCl subunits. Following an appropriate period of time to allow for expression, cellular protein is metabolically labelled with for example $^{35}$S-methionine for 24 hours, after which cell lysates and cell culture supernatants is harvested and subjected to immunprecipitation with polyclonal antibodies directed against the GluCl protein.

Other methods for detecting GluCl activity involve the direct measurement of GluCl activity in whole cells transfected with GluCl cDNA or oocytes injected with GluCl mRNA. GluCl activity is measured by specific ligand binding and electrophysiological characteristics of the host cells expressing GluCl DNA. In the case of recombinant host cells expressing GluCl patch voltage clamp techniques can be used to measure chloride channel activity and quantitate GluCl protein. In the case of oocytes patch clamp as well as two electrode voltage clamp techniques can be used to measure chloride channel activity and quantitate GluCl protein.

Levels of GluCl protein in host cells are quantitated by immunoaffinity and/or ligand affinity techniques. Cells expressing GluCl can be assayed for the number of GluCl molecules expressed by measuring the amount of radioactive glutamate or ivermectin binding to cell membranes. GluCl-specific affinity beads or GluCl-specific antibodies are used to isolate for example $^{35}$S-methionine labelled or unlabelled GluCl protein. Labelled GluCl protein is analyzed by SDS-PAGE. Unlabelled GluCl protein is detected by Western blotting, ELISA or RIA assays employing GluCl specific antibodies.

Because the genetic code is degenerate, more than one codon may be used to encode a particular amino acid, and therefore, the amino acid sequence can be encoded by any of a set of similar DNA oligonucleotides. Only one member of the set will be identical to the GluCl sequence but will be capable of hybridizing to GluCl DNA even in the presence of DNA oligonucleotides with mismatches under appropriate conditions. Under alternate conditions, the mismatched DNA oligonucleotides may still hybridize to the GluCl DNA to permit identification and isolation of GluCl encoding DNA.

DNA encoding GluCl frown a particular organism may be used to isolate and purify homologues of GluCl from other organisms. To accomplish this, the first GluCl DNA may be mixed with a sample containing DNA encoding homologues of GluCl under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either hi the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of GluCl is a compound that possesses a biological activity (either functional or structural) that is substantially similar to the biological activity of GluCl. The term "functional derivatives" is intended to include the "fragments," "variants," "degenerate variants," "analogs" and "homologues" or to "chemical derivatives" of GluCl. The term "fragment" is meant to refer to any polypeptide subset of GluCl. The term "variant" is meant to refer to a molecule substantially similar in structure and function to either the entire GluCl molecule or to a fragment thereof. A molecule is "substantially similar" to GluCl if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire GluCl molecule or to a fragment thereof.

Following expression of GluCl in a recombinant host cell, GluCl protein may be recovered to provide GluCl in active form. Several GluCl purification procedures are available and suitable for use. As described above for purification of GluCl from natural sources, recombinant GluCl may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant GluCl can be separated from other cellular proteins by use of an immunoaffinity column made with monoclonal or polyclonal antibodies specific for full length nascent GluCl, polypeptide fragments of GluCl or GluCl subunits.

Monospecific antibodies to GluCl are purified from mammalian antisera containing antibodies reactive against GluCl or are prepared its monoclonal antibodies reactive with GluCl using the technique of Kohler and Milstein, *Nature* 256: 495–497 (1975). Monospecific antibody as used herein is defined as a single antibody species or multiple antibody species with homogenous binding characteristics for GluCl. Homogenous binding as used herein refers to the ability of the antibody species to bind to a specific antigen or epitope, such as those associated with the GluCl, its described above. GluCl specific antibodies are raised by immunizing animals such as mice, rats, guinea pigs, rabbits, goats, horses and the like, with rabbits being preferred, with an appropriate concentration of GluCl either with or without an immune adjuvant.

Preimmune serum is collected prior to the first immunization. Each animal receives between about 0.1 mg and about 1000 mg of GluCl associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of GluCl in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with GluCl are prepared by immunizing inbred mice, preferably Balb/c, with GluCl. The mice are immunized by the IP or SC route with about 0.1 mg to about 10 mg, preferably about 1 mg, of GluCl in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of GluCl in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using GluCl as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies am produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-GluCl mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of GluCl in body fluids or tissue and cell extracts.

It is readily apparent to those skilled in the art that the above described methods for producing monospecific antibodies may be utilized to produce antibodies specific for GluCl polypeptide fragments, or full-length nascent GluCl polypeptide, or the individual GluCl subunits. Specifically, it is readily apparent to those skilled in the art that monospecific antibodies may be generated which are specific for only one GluCl subunit or the fully functional glutamate-gated/avermectin-gated chloride channel.

GluCl antibody affinity columns are made by adding the antibodies to Affigel-10 (Biorad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing GluCl or GluCl subunits are slowly passed through the column. The column is then washed with phosphate buffered saline until the optical density ($A_{280}$) falls to background, then the protein is eluted with 0.23 M glycine-HCl (pH 2.6). The purified GluCl protein is then dialyzed against phosphate buffered saline.

Two DNA clones, termed pGluClα and pGluClβ, are identified which encode proteins that, when expressed in Xenopus oocytes, form a chloride channel sensitive to glutamate and ivermectin-4-O-phosphate ($IVMPO_4$). Each subunit is capable of forming homomeric chloride channels that show distinctly different electrophysiological and pharmacological properties. When the GluClα and GluClβ subunits are coexpressed the resulting properties indicate an interaction of the two proteins to form heteromeric chloride channels in oocytes. The coexpression of GluCl α&β results in the reconstitution of the properties observed in oocytes injected with GluCl-encoding poly $(A)^+$ RNA [Arena, J. P., Liu, K. K., Paress, P. S. & Cully, D. F. Mol. Pharmacol. 40, 368–374 (1991)], [Arena, J. P., Liu, K. K., Paress, P. S., Schaeffer, J. M. & Cully, D. F. Mol. Brain Res. 15, 339–348 (1992)]. These include: direct activation of current with $IVMPO_4$, glutamate and ibotenate; desensitization in the presence of glutamate; potentiation of glutamate-sensitive cur..nt with $IVMPO_4$; an outwardly rectifying I/V relationship; low affinity block by picrotoxin and flufenamic acid; and insensitivity to GABA and glycine.

Glutamate-gated chloride channels have only been reported in invertebrates and are found on insect muscle and neuronal somata, crustacean muscle, and express in oocytes from insect muscle poly $(A)^+$ RNA [Lingle, C. & Marder, E. Brain Res. 212, 481–488 (1981)], [Horseman, B. G., Seymour, C., Bennudez, I. & Beadle, D. J. Neurosci. Lett. 85, 65–70 (1988)], [Wafford, K. A., & Sattelle, D. B. J. Exp. Biol. 144, 449–462 (1989)], [Lea, T. J. & Usherwood, P. N. R. Comp. Gen. Pharmacol. 4, 333–350 (1973)], [Cull-Candy, S. G. J. Physiol. 255, 449–464 (1976)]. [Fraser, S. P., et al. Mol. Brain Res. 8, 331–341 (1990)]. The terminology H (hyperpolarization) receptor is used to distinguish glutamate-gated chloride channels from the excitatory D (depolarization) glutamate receptors of locust muscle [Lea, T. J. & Usherwood, P. N. R. Comp. Gen. Pharmacol. 4, 333–350 (1973)], [Cull-Candy, S. G. J. Physiol. 255, 449–464 (1976)]. Similar to oocytes injected with GluCl α&β RNA, arthropod H-receptors are characteristically activated with ibotenate, blocked with low affinity by picrotoxin, and are not activated with GABA [Lingle, C. & Marder, E. Brain Res. 212, 481–488 (1981)], [Wafford, K. A. & Sattelle, D. B. J. Exp. Biol. 144, 449–462 (1989)], [Cull-Candy, S. G. J. Physiol. 255, 449–464 (1976)], [Lea, T. J. & Usherwood, P. N. R. Comp. Gen. Pharmacol. 4, 351–363 (1973)]. Locust muscle H-receptors are directly activated with avermectins as are the glutamate-gated chloride channels expressed from C. elegans poly $(A)^+$ RNA [Scott, R. H. & Duce, I. R. Pestic, Sci. 16, 599–604 (1985)], [Arena, J. P., Liu, K. K., Paress, P. S. Schaeffer, J. M. & Cully, D. F. Mol. Brain Res. 15, 339–348 (1992)]. In addition, glutamate-gated chloride channels on locust neuronal soma are potentiated, and directly activated by avermectin [Aydar, E., Harding, L., Beadle, D. J. & Bermudez, I. Proceedings of the British Pharmacological Society p24 (1993)]. Therefore, GluClα and GluClβ appear to represent a class of ligand-gated chloride channels related to arthropod H-receptors. This class of channels represents the target for avermectins in C. elegans, and may mediate the anthelmintic and insecticidal actions of avermectins in other organisms.

Phylogenetic analyses suggests that GluClα and GluClβ represent a unique subclass of ligand-gated chloride channels that may be related to the glycine α and β, Lym z and Dros rdl proteins. Although these proteins are phylogenetically related, they respond to different ligands and are pharmacologically distinct [Schmieden, V., Grenningloh, G., Schofield, P. R. & Betz, H. EMBO Journal 8, 695–700 (1989)], [ffrench-Constant, R. H., Rocheleau, T. A., Steichen, J. C. & Chalmers, A. E. Nature 363, 449–451 (1993)], [Grenningloh, G., et al. Neuron 4, 963–970 (1990)], [Hutton, M. L, Harvey, R. J. Earley, F. G. P., Barnard, E. A. & Darlison, M. G. FEBS letters 326, 112–116 (1993)]. The relatedness of the GluClα subunit to the GluClβ subunit is also reflected in the apparent conservation of binding sites for both glutamate and $IVMPO_4$. Homomeric GluClβ channels are directly activated with glutamate, but also bind $IVMPO_4$ since the activation of current by glutamate is inhibited after $IVMPO_4$. In homomeric GluClα channels, current directly activated with $IVMPO_4$ is further activated with glutamate, demonstrating a glutamate binding site on GluClα.

Avermectins have been reported to interact with other members of the ligand-gated chloride channel family. In nematodes and insects avermectins block GABA-sensitive current while in crayfish avermectins directly activate a multitransmitter-gated chloride channel (glutamate, acetylcholine, GABA) [Martin, R. J. & Pennington, A. J. Br. J. Pharmacol. 98, 747–756 (1989)], [Zufall, F., Franke, C. & Hatt, H. J. Exp. Biol. 142, 191–205 (1989)], [Holden-Dye, L. & Walker, R. J. Parasitology 101, 265–271 (1990)], [Bermudez, I., Hawkins, C. A., Taylor, A. M. & Beadle, D. J. Journal of Receptor Research 11, 221–232 (1991). In oocytes expressing chick brain $GABA_a$ receptors avermectins potentiate the GABA response [Sigel, E. & Baur, R. *Mol. Pharmacol.* 32, 749–752 (1987)]. In addition, avermectins inhibit strychnine binding to mammalian glycine receptors [Graham, D., Pfeiffer, F. & Betz, H. Neurosci. Letters 29, 173–176 (1982)]. However, GluClα and GluClβ proteins are the only members of the ligand-gated chloride channel family that show unique pharmacological characteristics with respect to glutamate and ibotenate, and therefore represent a new subclass of the ligand-gated ion channel family.

The present invention is also directed to methods for screening for compounds which modulate the expression of DNA or RNA encoding GluCl as well as the function of GluCl protein in vivo. Compounds which modulate these activities may be DNA, RNA, peptides, proteins, or non-proteinaceous organic molecules. Compounds may modulate by increasing or attenuating the expression of DNA or RNA encoding GluCl, or the function of GluCl protein. Compounds that modulate the expression of DNA or RNA encoding GluCl or the function of GluCl protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, insecticides and anthelminthics.

Kits containing GluCl DNA, antibodies to GluCl, or GluCl protein may be prepared. Such kits are used to detect DNA which hybridizes to GluCl DNA or to detect the presence of GluCl protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of GluCl DNA, GluCl RNA or GluCl protein. The recombinant proteins, DNA molecules, RNA molecules and antibodies lend themselves to the formulation of kits suitable for the detection and typing of GluCl. Such a kit would comprise a compartmentalized carrier suitable to hold in close confinement at least one container. The carrier would further comprise reagents such as recombinant GluCl protein or anti-GluCl antibodies suitable for detecting GluCl. The carrier may also contain a means for detection such as labeled antigen or enzyme substrates or the like.

Nucleotide sequences that are complementary to the GluCl encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other GluCl antisense oligonucleotide mimetics. GluCl antisense molecules may be introduced into cells by microinjection, liposome encapsulation or by expression from vectors harboring the antisense sequence. GluCl antisense therapy may be particularly useful for the treatment of diseases where it is beneficial to reduce GluCl activity.

GluCl gene therapy may be used to introduce GluCl into the cells of target organisms. The GluCl gene can be ligated into viral vectors which mediate transfer of the GluCl DNA by infection of recipient host cells. Suitable vital vectors include retrovirus, adenovirus, adeno-associated virus, herpes virus, vaccinia virus, polio virus and the like. Alternatively, GluCl DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo GluCl gene therapy. GluCl gene therapy may be particularly useful for the treatment of diseases where it is beneficial to elevate GluCl activity.

Pharmaceutically useful compositions comprising GluCl DNA, GluCl RNA, or GluCl protein, or modulators of GluCl receptor activity, may be formulated according to known methods such as by the admixture of a pharmaceutically acceptable carrier. Examples of such carriers and methods of formulation may be found in Remington's Phamaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of GluCl-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the GluCl receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient for use in the modulation of GluCl receptors can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a GluCl modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drag is ordinarily supplied at a dosage level of from about 0.0001 mg/kg to about 100 mg/kg of body weight per day. The range is more particularly from about 0.001 mg/kg to 10 mg/kg of body weight per day. The dosages of the GluCl receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyl-eneoxidepolyl-ysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds are antiparastic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uninaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have activity against these parasites, and in addition are also active against Dirofilaria in dogs, Nematospiroides and Syphacia in rodents, biting insects, and migrating diperous larvae such as *Hypoderma sp.* in cattle, and Gastrophilus in horses.

The compounds are also useful against endo and ecto parasites which cause parasitic diseases in humans. Examples of such endoparasites which infect man include gastro-intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The compounds are active against these endo and ecto parasites and in addition are also active against biting insects and other dipterous pests which annoy humans.

The compounds are also useful against common household pests such as *Blatella sp.* (cockroach), *Tineola sp.* (clothes moth), *Attagenus sp.* (carpet beetle), *Musca domestica* (housefly) and against Solenopsis Invicta (imported fire ant).

The compounds are furthermore useful against agricultural pests such as aphids (*Acyrthiosiphon sp.*), locusts, and boll weevils as well as against insect pests which attack stored grains such as *Tribolium sp.* and against immature stages of insects living on plant tissue. The compounds are also useful as a nematodicide for the control of soil nematodes which may be agriculturally important.

For use as an antiparasitic agent in animals the compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds is possible through the use of a liquid drench or a shampoo containing the instant compounds as an aqueous solution or suspension. These formulations generally contain a suspending agent such as bentonite and normally will also contain an anti-foaming agent. Formulations containing from 0.005 to 10% by weight of the active ingredient are acceptable. Preferred formulations are those containing from 0.01 to 5% by weight of the instant compounds.

The compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds may be used individually or in combination with each other or with other unrelated antiparasitic agents. The dosage of the compounds required for best results depends on several factors such as the species and size of the animal, the type and severity of the infection, the method of administration and the compound used. Oral administration of the compounds at a dose level of from 0.0005 to 10 mg per kg of animal body weight, either in a single dose or in several doses spaced a few days apart, generally gives good results. A single close of one of the compounds normally gives excellent control however repeat doses may be given to combat re-infection or for parasite species which are unusually persistent. The techniques for administering these compounds to animals are known to those skilled in the veterinary field.

The compounds may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples illustrate the present invention without, however, limiting the same thereto.

EXAMPLE 1

*C. elegans* RNA isolation

*C. elegans* cultures were maintained on *E. coli*-seeded agar petri dishes and isolated by flotation of 60% sucrose, as described by Sulston and Hodgkin [In: The Nematode *Caenorhabditis Elegans* p602–603 (1988) W. B. Wood editor, Cold. Spring Harbor Press, Cold Spring Harbor, N.Y., Publisher]. *C. elegans* preparations were rapidly frozen in liquid N2 and ground with a mortar and pestle while submerged in liquid N2. A solution containing 4 M guanidinium thiocyanate, 5 mM sodium citrate pH 7.0, and 0.1 M β-mercaptoethanol was mixed with a polytron homogenizer while the frozen powdered worms were added at 10 ml/g of worms. After 5 minutes of homogenization, 0.5% sodium sarkosyl was added and mixed well and the solution was centrifuged at 10,000 rpm for 10 minutes. The supernatant was layered over a 5.7 M CsCl cushion and centrifuged for 16 hours at 33,000 rpm. The RNA pellet was washed with 70% ethanol, resuspended in $H_2O$ and extracted with chloroform:isobutanol, 4:1 and precipitated with ethanol. Poly A (+) RNA was isolated by two rounds of purification on oligo (dT)-cellulose columns.

Agarose gel purification of poly A (+)RNA

Ultra low gelling temperature agarose (SeaPrep, FMC) was used to size fractionate poly A(+) RNA. Agarose (2%) was boiled in 15 mM $NaPO_4$, 1 mM EDTA, pH 6.5 and once fully dissolved, 15 mM iodoacetic acid (IAA) was added and the agarose was boiled an additional 2 minutes to inactivate any RNase present. All solutions were treated with 0.1% diethylpyrocarbonate for 12 hours and autoclaved for 15 minutes. The gel apparatus and preparative comb were soaked in 15 mM IAA for 12 hours and rinsed with DEP treated $H_2O$. The gel was cast and electrophoresed at 4° C. in 15 mM $NaPO_4$, 1 mM EDTA pH 6.5 and 6.5 V/cm with buffer circulation. The RNA was electrophoresed for approximately 20 hours or until the xylene cyanol was 7 cm into the gel. Approximately 1–2 mm slices of gel was taken from 7.5 cm into the gel up to the origin of the gel and numbered 1–47 (bottom to top).

RNA Size Fractionation

Approximately 150 μg of *C. elegans* poly A(+) RNA was ethanol precipitated and the dried pellet resuspended in 400 μl of formamide and denatured at 65° C. for 3 minutes, 50 μl of 1% SDS, 10 mM EDTA was added, mixed and the sample heated at 65° C. for 3 minutes. 50 μl of RNA loading buffer (50% glycerol 1 mM EDTA 0.4% BPB, 0.4% XC) was added and the sample immediately loaded.

RNA Recovery

The gel slices were added to 15 ml tubes and placed in a 65° C bath until melted. 10 ml of prewarmed 1x oligo dT binding buffer (BB) was added (0.5M KCl, 10 mM HEPES pH 7.5, 1 mM EDTA), the sample was mixed and brought to room temperature (about 23° C.). 1 g of oligo dT cellulose (Type 7, Pharmacia) was hydrated in 1x BB and resuspended in 15 ml of 1x BB with 1 ug/ml tRNA and 25 u/ml of RNasin (Promega). 200 μl of the oligo dT cellulose suspension was aliquoted into the melted agarose samples and rocked end-over-end for 1 hour. The sample was centrifuged, washed once with 1x BB and twice with 1x wash buffer (0.1 M KCl, 10 mM HEPES pH 7.5, and 1 mM EDTA). The sample was transferred to tubes and centrifuged at 10,000 x g, 1 minute and the pellet resuspended in 200 μl elution buffer (10 mM HEPES pH 7.5, 1 mM EDTA). The RNA was extracted with buffered phenol at 65° C., and $CHCl_3$ at 22° C., NaAcetate was added to 0.3 M with 1 μg of carrier tRNA and the RNA was precipitated with 2 volumes of ethanol. The ethanol precipitation was repeated and the RNA was stored until use at −20° C. as an ethanol precipitate.

EXAMPLE 2

Plasmid Preparation

The plasmid vector pBluescript SKII(+) was obtained from Stratagene. The plasmid (4 μg) was digested with 20 units of Not I and 24 units of EcoRV in 150 mM NaCl, 6 mM Tris-HCl pH 7.9, 6 mM $MgCl_2$, 1 mM DTT, in a volume of 46 μl, for 2 hours at 37° C. The enzymes were heat inactivated at 65° C. for 10 minutes and extracted twice with buffered phenol, twice with $CHCl_3$ and precipitated with 0.3 M NaAcetate and 2 volumes of 100% ethanol. The pellet was resuspended in 20.5 μl of water and 2.5 μl of 10x AP buffer (0.5 M Tris-HCl pH 9.0, 10 mM $MgCl_2$, 1 mM $ZnCl_2$, 10 mM spermidine) was added with 1 μl (1 unit) of alkaline phosphatase (Promega) and reacted for 30 minutes at 42° C. with an additional aliquot of 1 unit of AP added and reacted a further 30 minutes at 37° C. The sample was electrophoresed through 0.8% SeaKem LE agarose gel in TAE buffer (40 mM Tris-Acetate, 1 mM EDTA pit 8.3) and the linear vector DNA purified from the gel using the Clean Gene (Bio101).

Ligations

Approximately 75 ng of linear EcoRV-Not I digested pBluescript SK II(+) DNA was mixed with approximately 6 ng of cDNA from approximately 3.1 ml from the start of the CL6B column, in 15 μl and treated with 0.5 units of T4 DNA ligase (Boehringer Mannheim) for 16 hours at 16° C. The samples were precipitated with the addition of 7.5 μl of 8M $NH_4$ acetate and 2 volumes of 100% ethanol. The pellet was washed in 70% ethanol, dried and resuspended in 2 μl water.

EXAMPLE 3

CLONING OF pGluClα and pGluClb cDNA synthesis

FIRST STRAND SYNTHESIS: Approximately half of the RNA from fractions 21 and 22 were used to synthesize cDNA. The RNA precipitate was centrifuged and the pellet washed with 70% ethanol and dried by vacuum. The RNA pellet was resuspended in 25 μl of DEP treated $H_2O$, heated at 65° C. for 10 minutes. and placed on ice. The following reagents were added on ice: 2 μl of RNasin (40 u/μl), 1 μl Actinomycin D (800 μg/μl made fresh in 100% ethanol), 10 μl 5x RT buffer (250 mM Tris-HCl pH 8.3, 375 mM KCl, 15 mM $MgCl_2$, BRL), 5 μl of 0.1 M DTT, 5 μl 5 mM dNTPs, 2.8 μl of 11 ng/μl primer oligonucleotide 5'GAGAGAGAGAGAGAGAGAGAGCGGC-CGCTTTTTTTTTTTTTTTT TTTT3' (SEQ. ID. NO.:5), and 0.5 μl of 200 u/μl of Moloney Murine Leukemia virus reverse transcriptase. The reaction was incubated for 60 minutes at 37° C., extracted with phenol:CHCl$_3$(1:1, v:v, with Tris-HCl pH 7.4-buffered phenol, BRL) and purified on a sepharose G-50 column according to manufacturers specifications (Boehringer Mannheim).

SECOND STRAND SYNTHESIS: First strand product from G-50 column (Boehringer Mannheim) was adjusted to 55 μl and the following reagents were added at 4° C.: 10 μl of 10x 2nd strand buffer (200 mM Tris pH 7.4, 70 mM MgCl$_2$, 1M KCl), 5 μl BSA(1 mg/ml), 3 μl 5 mM dNTPs-(nucleotide triphosphates), 10 μl NAD (1.4 mM, pH 7.2, made with RNase free methods and stored at −20° C.), 5 μl aP$^{32}$dCTP (3000 Ci/mmol, 10.0 mCi/ml), 2.5 μl *E. Coli* ligase (NEBL 6 u/μl), 1.1 μl RNase H (1.1 u/μl Pharmacia), 7 μl DNA pol I (4 u/μl Pharmacia). The reaction was placed at 16° C. for 60 minutes, 22° C for 120 minutes, 65° C. for 10 minutes and placed on ice. The reaction was extracted twice with buffered phenol, twice with CHCl$_3$:isoamyl alcohol (24:1, v:v). A sample of 1 μl was removed for quantitation of cDNA synthesis and NaAcetate was added to 0.3M with 20 μg of glycogen (Boehringher Mannheim) and 2 volumes of 100% ethanol and the DNA precipitated at −20° C. The cDNA synthesis was quantitated by TCA precipitation. A 1:10 dilution was made after the second strand synthesis and 1 μl was added to 10 ml of Aquasol to estimate total radioactive material added. An aliquot of 1 μl was mixed with 50 μg of carrier DNA in 100 μl and 100 μl of 25% TCA and 0.1% Na pyrophosphate was added on ice for 15 minutes. The precipitate was collected by vacuum filtration on a GF-B glass filter that was previously soaked in 10% TCA and 0.1% Na pyrophosphate at 4° C. and the filters were washed with ice cold 10% TCA. The filters were added to vials containing 10 ml of Aquasol and the radioactivity quantitated. The estimated yield of cDNA from approximately one half of the RNA from fractions 21 and 22 was 282 ng.

DNA from second strand synthesis was treated with T4 DNA polymerase to blunt the DNA ends. The DNA pellet was resuspended in 25 μl of water and 31 μl of 10x T4 DNA polymerase buffer was added with 1.5 μl of 5 mM dNTPs, and 0.5 μl of T4 DNA polymerase. The reaction was placed at 37° C. for 30 minutes and stopped by the addition of 0.5 μl of 500 mM EDTA, extracted twice with buffered phenol:CHCl$_3$ (1:1), twice with CHCl$_3$ and precipitated with 0.3M NaAcetate and 2 volumes of 100% ethanol. The DNA pellet was resuspended in 17 μl of water and 0.2 μl of 1 mg/ml BSA and 2 μl of 10x Not I buffer (NEBL) and 0.4 μl (4 u) of Not I and incubated at 37° C. for 3 hours. The sample was extracted twice with buffered phenol: CHCl$_3$ (1:1), twice with CHCl$_3$ and precipitated with 0.3M NaAcetate and 2 volumes of 100% ethanol. The DNA precipitate was resuspended in 25 μl of water and heated at 65° C. for 5 minutes and quenched on ice, 2.5 μl of 5M NaCl was added and the sample applied to a sepharose CL6B column (0.7×22 cm) which was prequilibrated and run in 0.5 M NaCl, 10 mM Tris-HCl pH 7.4. and 1 mM EDTA. 100 μl samples were collected and monitored by Cherenkoff counts for fractions containing cDNA which was excluded from the column and eluted in the column void volume, approximately 3.1 ml. The cDNA was quantitated based on the specific activities obtained from TCA precipitation and estimating a measured 21% efficiency of Cherenkoff counting. The cDNA yield from the peak 8 fractions was estimated to be about 268 ng. Each of the 100 μl fractions were ethanol precipitated with 10 μg of glycogen and two volumes of 100% ethanol. The pellets were resuspended in 10 μl of water and extracted with buffered phenol: CHCl$_3$ (1:1), back extracted the phenol chloroform with 5 μl water and extracted twice with CHCl$_3$, add 1.5 μl of 3M NaAcetate and 16.5 μl of isopropanol at 22° C. was added. The pellet was collected by centrifugation, washed and dried and resuspended in 5 μl of water. DNA was electroporated into TOP10 *E.coli* cells (Invitrogen) and clones selected by growth in liquid media with ampicillin. DNA extracted from amplified libraries representing 2×10$^5$ recombinants were Not I digested and size separated by gel electrophoresis. The 4.0–4.7 Kb linear DNA was recovered (with Clean Gene, Bio101) and recloned in pools of 5000 recombinants. The 5000 colonies were plated on individual LB-Amp agar plates, grown overnight, scraped off in LB media, and ⅓rd was frozen at −70° C. as a bacterial stock and the rest used to prepare DNA with the Promega Wizard Miniprep system. The DNA was linearized with NotI and used to synthesize in vitro RNA.

EXAMPLE 4

Characterization Of pGluClα and pGluClb

*Xenopus laevis* oocytes were prepared and injected using standard methods previously described and known in the art [Arena, J. P., Liu. K. K., Paress, P. S. & Cully. D. F. *Mol. Pharmacol.* 40, 368–374 (1991 ); Arena, J. P., Liu, K. K., Paress, P. S., Schaeffer, J. M. & Cully, D. F. *Mol. Brain Res.* 15, 339–348 (1992)]. Adult female *Xenopus laevis* were anesthetized with 0.17% tricaine methanesulfonate and the ovaries were surgically removed and placed in a dish consisting of (mM): NaCl 1 82.5, KCl 2. MgCl$_2$ 1, CaCl$_2$ 1.8, HEPES 5 adjusted to pH 7.5 with NaOH (OR-2). Ovarian lobes were broken open, rinsed several times, and gently shaken in OR-2 containing 0.2% collagenase (Sigma, Type 1A) for 2–5 hours. When approximately 50% of the follicular layers were removed, Stage V and VI oocytes were selected and placed in media consisting of (mM): NaCl 86, KCl 2, MgCl$_2$ 1, CaCl$_2$ 1.8, HEPES 5, Na pyruvate 2.5, theophylline 0.5, gentamicin 0.1 adjusted to pH 7.5 with NaOH (ND-96) for 24–48 hours before injection. Oocytes were injected with 50–70 nl of poly(A$^+$) RNA (1 mg/ml) or 50 nl of GluClα (0.1–100 ng) and/or GluClβ (0.1–100 ng). Control oocytes were injected with 50 nl of water. Oocytes were incubated for 2–10 days in ND-96 before recording. Incubations and collagenase digestion were carried out at 18° C.

Recordings were made at room temperature 2–10 days after injection. Unless otherwise indicated recordings were made in standard frog saline consisting of (mM): NaCl 115, KCl 2, MgCl$_2$ 1, CaCl$_2$ 1.8, HEPES 10 adjusted to pH 7.5 with NaOH. Oocytes were voltage-clamped using a standard two microelectrode amplifier (Dagan 8500 or TEV-200, Minneapolis, Minn.). Pipettes were filled with 3M KCl and had resistances between 0.5–3.0 MΩ. A plexiglass recording chamber (volume 200 μl) was constantly perfused at a rate of 10 ml/min. The recording chamber was connected to ground with a Ag/AgCl electrode directly, or through a 3M KCl agar bridge when extracellular chloride was varied. For low chloride solutions NaCl was replaced with equimolar concentrations of sodium isethionic acid. For low sodium solutions NaCl was replaced with equimolar KCl or choline Cl. Data were acquired and analyzed using PCLAMP with a TL-1 interface (Axon Instruments, Foster City, Calif.). Membrane current at a holding potential of −80 mV was recorded. The amplitude of drug-sensitive current was determined by subtracting the holding current at −80 mV from from the peak current obtained in the presence of drug. Data were filtered at 30 Hz and sampled at 16.6 Hz. Current/ voltage relationships (I/V) and reversal potentials ($E_{rev}$) were determined using a 1–3 sec voltage ramp over the voltage range of −110 to +80 mV. For the ramps, data were filtered at 0.3–3 kHz and sampled at 160 Hz. Current in drug free solution was subtracted from current in the presence of drug to obtain drug-sensitive current/voltage relationships.

Xenopus oocytes injected with *C. elegans* poly(A)$^+$ RNA exhibited a rapidly activating reversible glutamate- and irreversible ivermectin 4-O-phosphate (IVMPO$_4$)-sensitive current (FIG. 5 [Arena, J. P., Liu, K. K., Paress, P. S., Schaeffer, J. M., & Cully, D. F. *Mol. Brain Res.* 15, 339–348 (1992); Arena, et al 1991 supra]. To isolate a functional cDNA clone for the glutamate- and IVMPO$_4$- sensitive channel a directional cDNA library was constructed from the 1.7–1.9 kB fraction of the size fractionated *C. elegans* poly (A)$^+$ RNA. Glutamate and IVMPO$_4$-sensitive currents were observed after injection of in vitro RNA synthesized from a pool of 5000 cDNAs. Subfractionation of this population of cDNAs into smaller pools indicated that two different subunits were necessary for recovering the glutamate and IVMPO$_4$ responses. Two pools of 500 cDNAs were identified that, when added together, recovered both responses. The cDNA clone pGluClα, was isolated by coinjection of RNA from a subfractionated pool with RNA from a second pool of 500 cDNAs. The cDNA clone pGluClβ was isolated by subfractionation of the second pool of 500 clones and coinjection with in vitro RNA from pGluCla. When the complexity of the subfractionated pools were reduced to 25 cDNAs it was possible to identify responses in oocytes injected with a single pool.

Electrophysiological properties were examined in oocytes injected with in vitro RNA from pGluClα and pGluClβ (FIG. 5). Oocytes simultaneously expressing GluCl α&β proteins exhibited the rapidly activating reversible glutamate- and irreversible IVMPO$_4$-sensitive current found in poly(A)$^+$ RNA injected oocytes (FIG. 5). The time for maximal activation of IVMPO$_4$-sensitive current was 42±2 seconds for GluCl α&β and 36±3 seconds for poly(A)$^+$ RNA. The desensitization of the glutamate-sensitive current seen in poly(A)$^+$ RNA injected oocytes was also observed in GluCl α&β injected oocytes at glutamate concentrations greater than 1 mM. The individual subunits, GluClα or GluClβ, expressed functional homomeric channels that were selectively responsive to IVMPO$_4$ or glutamate, respectively (FIG. 5). The time course for IVMPO$_4$ activation of homomeric GluClα channels was 18±1 seconds, faster than that observed for GluCl α&β or poly(A)$^{+ RNA}$ ($P$<0.001). GluClα channels were insensitive to glutamate concentrations as high as 10 mM, while the threshold for activation of homomeric GluClβ channels with glutamate was 50 µM. It was necessary to inject 10 times more RNA of the individual subunits to achieve currents with amplitudes comparable to coinjected oocytes, suggesting that functional formation of homomeric channels is less efficient.

Analysis of the glutamate and IVMPO$_4$ dose response curves indicated that the coexpression of GluCl α&β resulted in changes in ligand affinity and Hill coefficient (FIG. 5). Coinjection of GluClα with GluClβ resulted in a shift in the EC$_{50}$ for glutamate from 380 to 1360 µM (FIG. 1*b*). The Hill coefficients of 1.9 for G$_{lu}$Clβ and 1.7 for GluCl α&β suggest that more than one glutamate molecule is necessary to gate the channels. The EC$_{50}$ for IVMPO$_4$ activation of current was similar in GluClα and GluCl α&β injected oocytes with values of 140 and 190 nM, respectively (FIG. 5). However, the Hill coefficient was altered from 1.5 for GluClα to 2.5 for GluCl α&β, suggesting an increase in the number of IVMPO$_4$ molecules necessary to open the channel. The changes observed in EC$_{50}$ and Hill coefficient cannot be due to activation GluClα channels with glutamate or activation of GluClβ channels with IVMPO$_4$ since these homomeric channels do not respond to these ligands (FIG. 5).

Figure 6C:
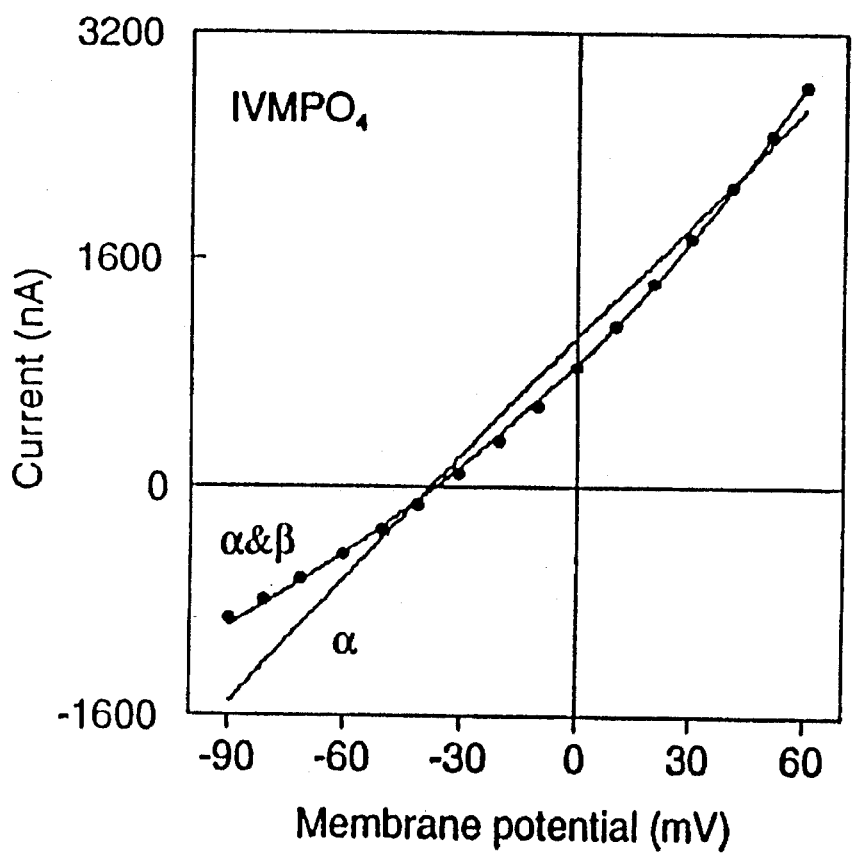

The permeability properties and current voltage relationship in oocytes expressing GluCl α&β channels were similar to that observed in poly(A)$^+$ RNA injected oocytes (FIG. 6) [Arena, J. P., Liu, K. K., Paress, P. S. & Cully, D. F. *Mol. Pharmacol.* 40, 368–374 (1991); Arena, J. P., Liu, K. K., Paress, P. S., Schaeffer, J. M. & Cully, D. F. *Mol. Brain Res.* 15, 339–348 (1992)]. The GluCl α&β channels were selective for chloride, as shown by the shift in the reversal potential ($E_{rev}$) for glutamate- or IVMPO$_4$-sensitive current after replacement of external NaCl with Na isothionate (FIG. 6). The GluCl α&β channels were not permeable to monovalent cations since replacement of external NaCl with KCl or choline Cl did not shift $E_{rev}$ (FIG. 6). Permeability studies for homomeric GluClα or GluClβ channels also revealed selectivity for anions over cations (FIG. 6). In both GluClα and GluClβ channels, replacement of NaCl with Na isothionate shifted the $E_{rev}$ to positive voltages, while replacement with KCl or choline Cl had no effect on $E_{rev}$ (FIG. 6). The $E_{rev}$ for GluClα channels in Na isothionate indicated that there was permeability to the large anion isothionate with a ratio to chloride of 0.2 [Goldman, D. E. *J. Gen. Physiol.* 27, 37–60 (1943); Hodgkin, A. L. & Katz B. *J. Physiol.* (*Lond.*) 108, 37–77 (1949)].

The current voltage relationship (I/V) in GluCl α&β injected oocytes showed an outwardly rectifying voltage dependence (FIG. 6). The I/V for glutamate- or IVMPO$_4$-sensitive currents showed similar voltage-dependence as confirmed by fits of the data to the constant field equation (FIG. 6) [Goldman, D. E. . *J. Gen. Physiol.* 27, 37–60 (1943)], [Hodgkin, A. L. & Katz B. *J. Physiol.* (*Lond.*) 108, 37–77 (1949)]. The I/V curves for the homomeric GluClα or GluClβ channels deviated strongly from the I/V curve for GluCl α&β and were not fit well by constant field assumptions (FIG. 6). The glutamate-sensitive current from GluClβ channels exhibited a steep outwardly rectifying voltage dependence with small currents at negative voltages (FIG. 6). The IVMPO$_4$-sensitive current from GluClα channels showed essentially a linear voltage dependence (FIG. 6).

Figure 7G:
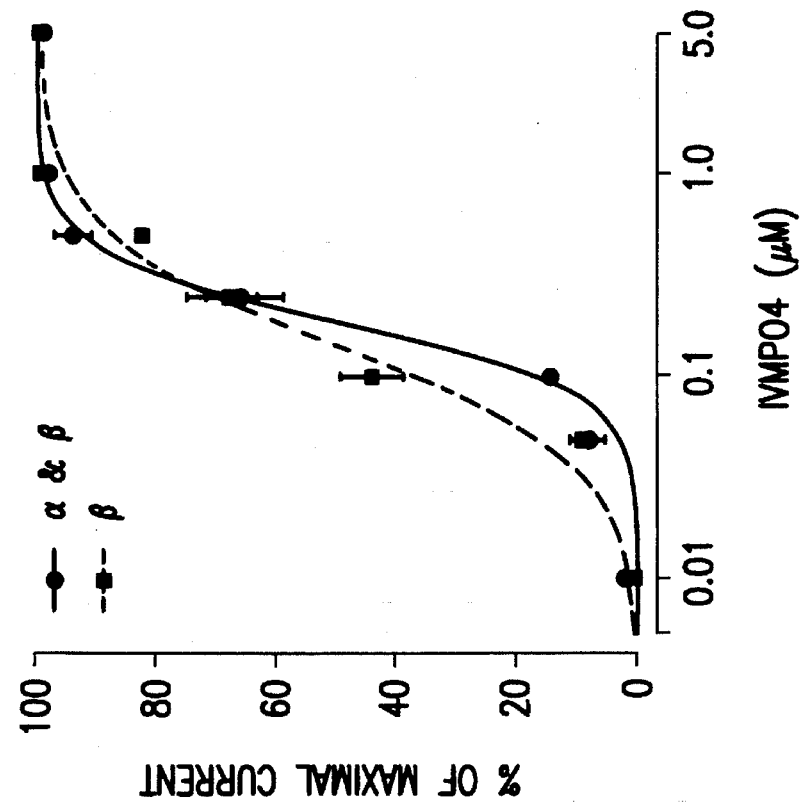
Figure 7F:
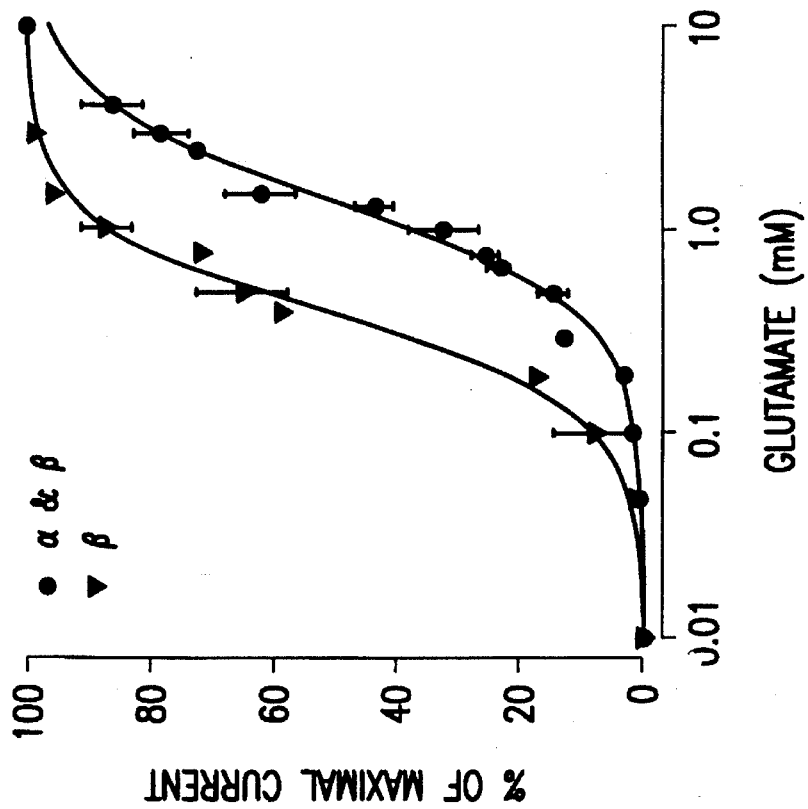
Figure 8:
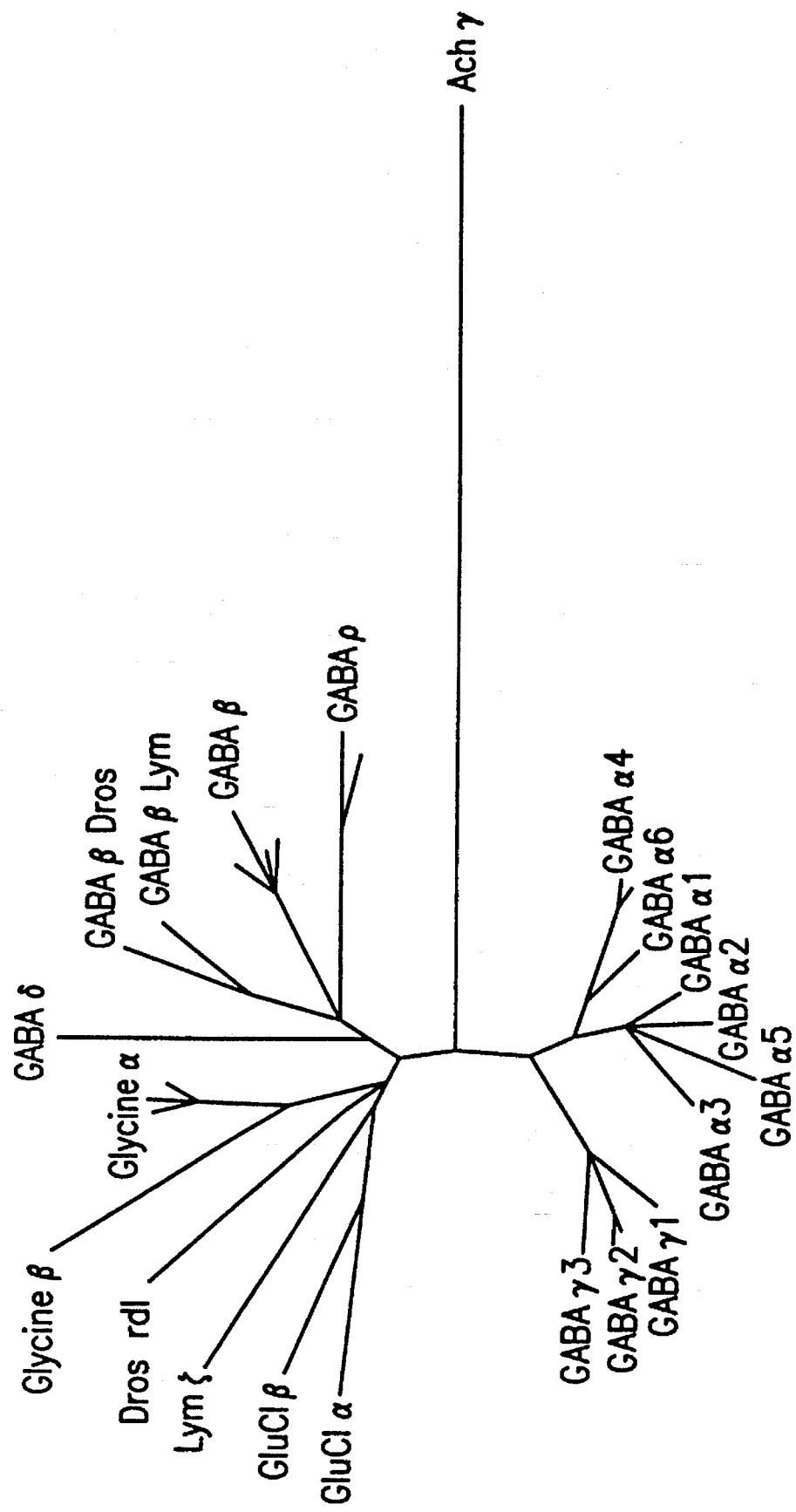

IVMPO$_4$ has a dual effect on oocytes injected with *C. elegans* poly (A)$^+$ RNA [Arena, J. P., Liu, K. K., Paress, P. S. & Cully, D. F. *Mol. Pharmacol.* 40, 368–374 (1991)], [Arena, J. P., Liu, K. K., Paress, P. S., Schaeffer, J. M. & Cully, D. F. *Mol. Brain Res.* 15, 339–348 (1992)]. In addition to direct activation of current (FIG. 5), the glutamate-sensitive current is potentiated by low concentrations of IVMPO$_4$ (FIG. 7) [Arena. J. P., Liu, K. K., Paress, P. S., Schaeffer, J. M. & Cully, D. F. *Mol. Brain Res.* 15, 339–348 (1992)]. Likewise, IVMPO$_4$ (5 nM) potentiated the glutamate-sensitive current 490±45% in GluCl α&β injected oocytes (FIG. 7). Coapplication of IVMPO$_4$ and glutamate shifted the EC$_{50}$ for glutamate from 1360 to 360 µM and reduced the Hill coefficient from 1.7 to 1.3. The glutamate response from homomeric GluClβ channels was not potentiated with IVMPO$_4$ (FIG. 7). In contrast, following higher concentrations of IVMPO$_4$ (1 µM), the glutamate-sensitive current was reduced 88±4% in GluClβ injected oocytes (FIG. 7). In oocytes expressing GluClα channels, which do not respond to glutamate (FIG. 5), prior activation of current with IVMPO$_4$ resulted in a 20±4% increase in current with glutamate (FIG. 7). The glutamate-sensitive current from GluClα injected oocytes was only observed following IVMPO$_4$ current activation, and could be observed with glutamate concentrations as low as 10 µM.

The pharmacological profile of GluCl α&β injected oocytes was distinct from all other cloned ligand-gated chloride channels and glutamate-gated cation channels (Table 1). Several ligand-gated ion channel agonists and antagonists were tested on oocytes injected with GluCl α&β (Table 1). All compounds were inactive except for ibotenate, a structural analog of glutamate, which is known to activate glutamate-sensitive chloride channels [Cull-Candy, S. G. *J. Physiol.* 255, 449–464 (1976); Arena, J. P., Liu, K. K., Paress, P. S., Schaeffer, J. M. & Cully, D. F. *Mol. Brain Res.* 15, 339–348 (1992); Lea, T. J. & Usherwood, P. N. R. *Comp. Gen. Pharmacol.* 4, 351–363 (1973)]. Glutamate- and IVMPO$_4$-sensitive currents were blocked with picrotoxin and flufenamic acid with a concentration-dependence similar to that reported for *C. elegans* poly (A)$^+$ RNA [Arena, J. P., Liu, K. K., Paress, P. S. & Cully, D. F. *Mol. Pharmacol.* 40, 368–374 (1991); Arena, J. P., Liu, K. K., Paress, P. S., Schaeffer, J. M. & Cully, D. F. *Mol. Brain Res.* 15, 339–348 (1992)].

Several lines of evidence indicated that coexpression of GluCl α&β leads to formation of heteromeric channels. The first indication of subunit association was during the cloning procedure where two pools of cDNAs were required to elicit responses. Secondly, it is necessary to inject 10 times more RNA of the individual subunits to achieve the expression level obtained with coinjected oocytes. In addition, the following changes in ligand-specific responses were observed in oocytes coexpressing GluCl α&β: the time course of IVMPO$_4$ activation of current; the affinity for glutamate and Hill coefficient of IVMPO$_4$ activation of current; differences in the rectification of the I/V relationship; the permeability to isethionate; and IVMPO$_4$ potentiation of the glutamate response. The identical voltage dependence of the glutamate- and IVMPO$_4$-sensitive I/V curves in coinjected oocytes strongly suggests that the majority of the channels formed are heteromeric. If significant numbers of homomeric GluClα and GluClβ channels were present in coinjected oocytes, then the glutamate sensitive I/V curve would be more outwardly rectifying than the I/V tbr IVMPO$_4$-sensitive current. These results suggest that the properties observed in coinjected oocytes represent the properties of heteromeric channels.

TABLE 1

| A. Agonists | | |
| --- | --- | --- |
| Compound | Conc. (mM) | % of Glutamate 10 mM[a] |
| GABA | 10 | NR[b] |
| Muscimol | 1 | NR |
| D-glutamate | 10 | 1 ± 2 |
| NMDA[c] | 1 | NR |
| Kainate | 1 | NR |
| L-aspartate | 10 | NR |
| Ibotenate | 0.5 | 18 ± 2 |
| Quisqualate | 1 | NR |
| AMPA[d] | 1 | NR |
| Glycine | 10 | NR |
| Histamine | 10 | NR |
| β-alanine | 10 | NR |
| Taurine | 10 | NR |
| Acetylcholine | 1 | NR |
| IVMPO$_4$ | 1 µM | 117 ± 13 |

| B. Antagonists | | | |
| --- | --- | --- | --- |
| Compound | Conc (µM) | Ligand | % Block[e] |
| Picrotoxin | 100 | Glutamate 1 mM | 68 ± 4 |
| Picrotoxin | 100 | IVMPO$_4$ 1 µM | 61 ± 2 |

TABLE 1-continued

| | | | |
| --- | --- | --- | --- |
| Flufenamic Acid | 200 | IVMPO$_4$ 1 µM | 60 ± 4 |
| Strychnine | 100 | Glutamate 1 mM | 0 |
| Bicuculline[f] | 100 | Glutamate 1 mM | 0 |
| CNQX[g] | 10 | Glutamate 1 mM | 0 |

Oocytes were injected simultaneously with GluClα and GluClβ RNA (25 pg each). n= at least four for each group. a- Data are expressed as % of the response elicited with 10 mM glutamate. b- NR= no response. c- N-methyl-D-aspartate. d- a-amino3-hydroxyl-5-methyl-4-isoxazole propionic acid. e- Block was considered zero if response in the presence of blocker was ± 3% of control. f- (-)-Bicuculline methochloride g. - 6-cyano-7-nitroquino-xaline-2,3-dione.

EXAMPLE 5

Glutamate and ivermectin binding assay on GluCl RNA injected oocytes

Oocytes injected with GluClα and GluClβ in vitro RNA were used in $^3$H-ivermectin and $^3$H-glutamate binding assays. GluClα (1 ng) or GluClβ RNA (1 ng) were injected into oocytes individually, or coinjected (0.5 ng each) and 2 days later the oocytes were disrupted with a dounce homogenizer and yolk proteins removed using standard methods known in the art. Equilibrium ligand binding assays were performed using conventional procedures. Oocytes expressing both GluCl α&β or GluClα both bound $^3$H-ivermectin with high affinity, approximately 0.2 nM. Specific $^3$H-glutamate binding was observed in membrane preparations from GluClα-injected oocytes. Oocytes expressing GluCl α&β are used to measure the affinity of binding of othere compounds and their ability to displace $^3$H-ivermectin and $^3$H-glutamate binding.

EXAMPLE 6

Primary Structure Of The GluClα And GluClβ Channels

The nucleotide sequences of pGluClα and pGluClβ revealed single large open reading frames of about 1383 and about 1302 base pairs. The cDNAs have 5' and 3'-untranslated extensions of about 50 and about 90 nucleotides for pGluClα, and about 13 and about 144 nucleotides for pGluClβ, respectively. The nucleotide sequence in the open reading frame regions of pGluClα and pGluClβ shared approximately 50% identity. The first in-frame methionines were designated as the initiation codons for open reading frames that predict a GluClα protein with an estimated molecular mass ($M_r$) of about 52,550 and a GluClβ protein with an estimated $M_r$ of about 49,900. Both proteins contained hydrophobic amino-terminal residues with sequences highly predictive of signal cleavage sites that would result in mature proteins initiating at amino acid 21 in GluClα and 23 in GluClβ. Comparison of the GluClα and GluClβ proteins showed 45% amino acid identity and 63% similarity.

The predicted GluClα and GluClβ proteins were aligned with nucleotide and protein databases and found to be related to the glycine and GABA$_a$ receptors. Approximately 21% of the amino acids in GluClα and GluClβ were highly conserved, showing at least 75% amino acid identity within the family of ligand-gated chloride channels. The conserved motifs found in this family of channels, such as a large NH$_2$-terminal extracellular domain and the four hydrophobic transmembrane domains M1 through M4, were also found in the GluClα and GluClβ sequences. The GluClα and GluClβ proteins contained the conserved cysteine residues found in the extracellular domain of all ligand-gated chloride channels (amino acids 191 and 205 in GluCla, and 161 and 175 in GluClb). Two additional cysteine residues were present that are also found in glycine-gated chloride channels (amino acids 252 and 263 in GluClα and amino acids 223 and 234 in GluClb). The GluClα protein contained a strong consensus sequence for a protein kinase C phosphorylation site located between the putative membrane spanning domains M3 and M4. In GABA$_a$ receptor subunits, similar phosphorylation sites are located in the intracellular domain between M3 and M4 and are believed to play a role in channel regulation [Leidenheimer, N. J., McQuilkin, S. J., Hahner, L. D., Whiting, P. & Harris, R. A. *Mol. Pharm.* 41, 1116–1123 (1992), [Kellenberger, S., Malherbe, P. & Sigel, E. *J. Biol. Chem.* 267, 24660– 25663 (1992)]. As found in GABA$_A$ and glycine receptor sequences, the GluClα and GluClβ proteins contained putative N-linked glycosylation sites in the proposed extracellular domain. Alignment analyses with the acetylcholine and glutamate cation channel subunits showed that GluClα and GluClβ share approximately 10% and <5% similarity, respectively.

A phylogenetic analysis was performed with the entire GluClα and GluClβ protein sequences, the GABA$_a$ and glycine receptor subunits, and related invertebrate protein sequences. A discrete evolutionary division in this family of proteins was shown by a divergence into two major branches resulting in the division of the GABA$_A$ α and γ subunits from the remaining proteins. Within these major branches are subbranches that group the proteins into the respective subclasses, such as the GABA$_a$ α, β, γ, delta (d), rho (r), and glycine α and β. The *Drosophila melanogaster* (Dros) and *Lymnae stagnalis* (Lym) sequences represent the available invertebrate protein sequences that am similar to the ligand-gated anion channels. The *C. elegans* GluClα and GluClβ protein sequences are loosely grouped on the same branch with the glycine α and β, Lym zeta (ζ) and Dros rdl proteins, suggesting that these proteins originated from a common ancestor. The GluClα and GluClβ proteins are most related to the glycine a proteins, as indicated by the shortest joining limb lengths. This analysis suggests that GluClα and GluClβ proteins form an independent subbranch separate from the other proteins. Similar phylogenetic trees were obtained using a maximum parsimony program or when the extracellular or membrane spanning domains of GluClα or GluClβ were analyzed separately.

Although the GluClα and GluClβ proteins are phylogenetically related to the glycine α and β, Lym ζ and Dros rdl proteins, they are pharmacologically distinct. Expression studies in Xenopus oocytes show that functional homomeric chloride channels are formed by the glycine α proteins that are sensitive to glycine [Schmieden, V., Grenningloh, G., Schofield, P. R. & Betz, H. *EMBO Journal* 8, 695–700 (1989)] and the Dros rdl protein that is sensitive to GABA [ffrench-Constant, R. H., Rocheleau, T. A., Steichen, J. C. & Chalmers. A. E. *Nature* 363, 449–451 (1993)]. Homomeric glycine b channels are formed at very low efficiency [Grenningloh, G., et al. *Neuron* 4, 963–970 (1990)], and the Lym ζ protein does not form functional homomeric channels [Hutton, M. L., Harvey, R. J., Earley, F. G. P., Barnard, E. A. & Darlison, M. G. *FEBS letters* 326, 112–116 (1993)]. Since GluClα and GluClβ homomeric channels are insensitive to GABA, glycine and related channel agonists and antagonists (see Table 1 ), these channels appear to have evolved distinct ligand selectivity, separate from their phylogenetically related channels.

Hybridization analysis was performed with *C. elegans* genomic DNA and poly A$^+$ RNA using the GluClα and GluClβ cDNAs as probes. High stringency hybridization of the cDNA probes with restriction digested genomic DNA showed that the GluCl cDNAs only hybridize to a single copy DNA fragment. High stringency hybridization to *C. elegans* RNA showed that GluClα hybridized to a 2.4 and 1.7 Kb RNA and GluClβ hybridized to a 1.7 Kb RNA. The probes used for this study represent only the regions of the GluClα and GluClβ cDNAs that encode the single large open reading frames. The GluClα and GluClβ probes were hybridized to a *C. elegans* YAC and cosmid library. This hybridization showed that the GluClα gene is located on chromosome V, on YAC # Y42B4 and cosmid # C25D4. The GluClβ gene is located on chromosome I, YAC # Y24C9 and cosmid # C04E4. The YAC and Cosmid classification is from John Sulston, MRC labs, Cambridge, England.

EXAMPLE 7

Cloning of the GluCl cDNA into *E. coli* Expression Vectors

Recombinant GluCl is produced in *E. coli* following the transfer of the GluCl expression cassette into *E. coli* expression vectors, including but not limited to, the pET series (Novagen). The pET vectors place GluCl expression under control of the tightly regulated bacteriophage T7 promoter. Following transfer of this construct into an *E. coli* host which contains a chromosomal copy of the T7 RNA polymerase gene driven by the inducible lac promoter, expression of GluCl is induced when an approriate lac substrate (IPTG) is added to the culture. The levels of expressed GluCl are determined by the assays described above.

The cDNA encoding the entire open reading frame for GluCl α and β is inserted into the NdeI site of pET [16 ]11a. Constructs in the positive orientation are identified by sequence analysis and used to transform the expression host strain BL21. Transformants are then used to inoculate cultures for the production of GluCl protein. Cultures may be grown in M9 or ZB media, whose formulation is known to those skilled in the art. After growth to an OD$_{600}$=1.5, expression of GluCl is induced with 1 mM IPTG for 3 hours at 37° C.

EXAMPLE 8

Cloning of GluCl cDNA into a Mammalian Expression Vector

The GluCl cDNAs were cloned into the mammalian expression vectors pMAMneo and pcDNA3. The GluClα and GluClβ Bluescript plasmids were digested with Not I and treated with Klenow enzyme to create a blunt cloning end. The inserts were excised with Sal I digestion and purified by agarose gel electrophoresis. The pMAMneo vector was treated with XhoI, Klenow enzyme and then SalI and calf intestinal phosphatase (CIP). The linear vector was purified on agarose gel and used to ligate to the GluCl cDNA inserts. Recombinants were isolated, designated GluClα-pMAMneo and GluClβ-pMAMneo, and used to transfect mammalian cells (L-cells) by CaPO$_4$-DNA precipitation. Cells were transfected with GluClα-pMAMneo, GluClβpMAMneo or both GluClα-pMAMneo and GluClβ-pMAMneo. Stable cell clones were selected by growth in the presence of G418. Single G418 resistant clones were isolated and shown to contain the intact GluClα or GluClβ gene or both GluClα or GluClβ genes. Clones containing the GluCl cDNAs are analyzed for expression using immunological techniques, such as immuneprecipitation, Western blot, and immunofluorescence using antibodies specific to the GluCl proteins. Antibody is obtained from rabbits innoculated with peptides that are synthesized from the amino acid sequence predicted from the GluCl sequences. Expression is also analyzed using patch clamp electrophysiological techniques, and $^3$H-ivermectin and $^3$H-glutamate binding assays.

The GluClα or GluClβ genes were inserted into pcDNA3. GluClα-Bluescript SKII+ and GluClβ-Bluescript SKII+ were digested with XhoI and NotI and the cDNA inserts isolated by agarose gel electrophoresis. The vector, pcDNA3, was digested with XhoI and NotI, treated with CIP and the linear vector isolated by gel electrophoresis, and ligated with cDNA inserts. Recombinant plasmids GluClα-pcDNA3 and GluClβ-pcDNA3 are used to transform the mammalian COS or CHO cells.

Cells that are expressing GluClα or GluClβ and GluClα & β, stably or transiently, will be used to test for expression of avermectin and glutamate-sensitive chloride channels and for ligand binding activity. These cells are used to identify and examine other compounds for their ability to modulate, inhibit or activate the avermectin and glutamate-sensitive chloride channel and to compete for radioactive ivermectin or glutamate binding.

Cassettes containing the GluCl cDNA in the positive orientation with respect to the promoter are ligated into appropriate restriction sites 3' of the promoter and identified by restriction site mapping and/or sequencing. These cDNA expression vectors are introduced into fiboblastic host cells for example COS-7 (ATCC#CRL1651), and CV-1 tat [Sackevitz et al., Science 238:1575 (1987)], 293, L (ATCC# CRL6362)] by standard methods including but not limited to electroporation, or chemical procedures (cationic liposomes, DEAE dextran, calcium phosphate). Transfected cells and cell culture supernatants can be harvested and analyzed for GluCl expression as described herein.

All of the vectors used for mammalian transient expression can be used to establish stable cell lines expressing GluCl. Unaltered GluCl cDNA constructs cloned into expression vectors are expected to program host cells to make GluCl protein. In addition, GluCl is expressed extracellularly as a secreted protein by ligating GluCl cDNA constructs to DNA encoding the signal sequence of a secreted protein. The transfection host cells include, but are not limited to, CV-1-P [Sackevitz et al., Science 238: 1575 (1987)], tk-L [Wigler, et al. Cell 11: 223 (1977)], NS/O, and dHFr- CHO [Kaufman and Sharp, J. Mol. Biol. 159: 601, (1982)].

Co-transfection of any vector containing GluCl cDNA with a drug selection plasmid including, but not limited to G418, aminoglycoside phosphotransferase; hygromycin, hygromycin-B phospholransferase; APRT, xanthine-guanine phosphoribosyl-transferase, will allow for the selection of stably transfected clones. Levels of GluCl are quantitated by the assays described herein.

GluCl cDNA constructs are also ligated into vectors containing amplifiable drug-resistance markers for the production of mammalian cell clones synthesizing the highest possible levels of GluCl. Following introduction of these constructs into cells, clones containing the plasmid are selected with the appropriate agent, and isolation of an over-expressing clone with a high copy number of plasmids is accomplished by selection in increasing doses of the agent.

The expression of recombinant GluCl is achieved by transfection of full-length GluCl cDNA into a mammalian host cell.

EXAMPLE 9

Cloning of GluCl cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing GluCl cDNA is produced by the following standard methods (In Vitrogen Maxbac Manual): the GluCl cDNA constructs are ligated into the polyhedrin gene in a variety of baculovirus transfer vectors, including the pAC360 and the BlueBac vector (In Vitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, GluCl expression is measured by the assays described herein.

The cDNA encoding the entire open reading frame for GluCl subunits is inserted into the BamHI site of pBlueBacII. Constructs in the positive orientation are identified by sequence analysis and used to transfect Sf9 cells in the presence of linear AcNPV mild type DNA.

Authentic, active GluCl is found in the cytoplasm of infected cells. Active GluCl is extracted from infected cells by hypotonic or detergent lysis.

EXAMPLE 10

Cloning of GluCl cDNA into a yeast expression vector

Recombinant GluCl is produced in the yeast *S. cerevisiae* following the insertion of the optimal GluCl cDNA cistron into expression vectors designed to direct the intracellular or extracellular expression of heterologous proteins. In the case of intracellular expression, vectors such as EmBLyex4 or the like are ligated to the GluCl cistron [Rinas, U. et al., Biotechnology 8: 543–545 (1990); Horowitz B. et al., J. Biol. Chem. 265: 4189–4192 (1989)]. For extracellular expression, the GluCl cistron is ligated into yeast expression vectors which fuse a secretion signal (a yeast or mammalian peptide) to the NH$_2$ terminus of the GluCl protein [Jacobson, M. A., Gene 85: 511–516 (1989); Riett L. and Bellon N. Blochem. 28: 2941–2949 (1989)].

These vectors include, but are not limited to pAVE1>6, which fuses the human serum albumin signal to the expressed cDNA [Steep O. Biotechnology 8: 42–46 (1990)], and the vector pL8PL which fuses the human lysozyme signal to the expressed cDNA [Yamamoto, Y., Biochem. 28: 2728–2732)]. In addition, GluCl is expressed in yeast as a fusion protein conjugated to ubiquitin utilizing the vector pVEP [Ecker, D. J., J. Biol. Chem. 264: 7715–7719 (1989), Sabin, E. A., Biotechnology 7: 705–709 (1989), McDonnell D. P., Mol. Cell Biol. 9: 5517–5523 (1989)]. The levels of expressed GluCl are determined by the assays described herein.

EXAMPLE 11

Purification of Recombinant GluCl

Recombinantly produced GluCl may be purified by antibody affinity chromatography.

GluCl antibody affinity columns are made by adding the anti-GluCl antibodies to Affigel-10 (Biorad), a gel support which is preactivated with N-hydroxysuccinimide esters such that the antibodies form covalent linkages with the agarose gel bead support. The antibodies are then coupled to the gel via amide bonds with the spacer arm. The remaining activated esters am then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized GluCl or GluCl subunits are slowly passed through the column. The column is then washed with phosphate- buffered saline together with detergents until the optical density (A280) falls to background, then the protein is eluted with 0.23M glycine-HCl (pH 2.6) together with detergents. The purified GluCl protein is then dialyzed against phosphate buffered saline.

What is claimed is:

1. An isolated and purified DNA molecule, having a nucleotide sequence selected from the group consisting of (SEQ.ID.NO.:1); and (SEQ.ID.NO.:2).

2. The isolated and purified DNA molecule of claim 1, wherein said DNA molecule is genomic DNA.

3. An expression vector, wherein the expression vector contains a cloned gene encoding an avermectin and/or glutamate binding protein, having a nucleotide sequence selected from the group consisting of: (SEQ.ID.NO.: 1); and (SEQ.ID.NO.:2).

4. The expression vector of claim 3, wherein the expression vector contains genomic DNA encoding an avermectin and/or glutamate binding protein wherein said protein functions as a glutamate-gated anion channel.

5. A recombinant host cell wherein said host cell contains a vector comprising a nucleotide sequence selected from the group consisting of (SEQ.ID.NO.:1); and (SEQ.ID.NO.:2).

6. The recombinant host cell of claim 5, wherein said cloned gene encoding a glutamate-gated anion channel is genomic DNA.

* * * * *